(12) United States Patent
Maeda et al.

(10) Patent No.: US 8,702,700 B2
(45) Date of Patent: Apr. 22, 2014

(54) SURGICAL TREATMENT DEVICE

(71) Applicants: Terumo Cardiovascular Systems Corporation, Ann Arbor, MI (US); Olympus Medical Systems Corp., Tokyo (JP)

(72) Inventors: Seiji Maeda, Higashiyamoto (JP); Hideyuki Kasahara, Hamura (JP); Akihito Kano, Hamburg (DE); Hiroaki Ichikawa, Yokohama (JP); Susumu Komagata, Ebina (JP); Randal J. Kadykowski, South Lyon, MI (US)

(73) Assignees: Terumo Cardiovascular Systems Corporation, Ann Arbor, MI (US); Olympus Medical Systems Corporation, Tokyo (JP)

( * ) Notice: Subject to any disclaimer, the term of this patent is extended or adjusted under 35 U.S.C. 154(b) by 0 days.

(21) Appl. No.: 13/662,634

(22) Filed: Oct. 29, 2012

(65) Prior Publication Data

US 2013/0060249 A1   Mar. 7, 2013

Related U.S. Application Data

(63) Continuation of application No. PCT/JP2011/073991, filed on Oct. 19, 2011.

(60) Provisional application No. 61/394,802, filed on Oct. 20, 2010.

(51) Int. Cl.
    *A61B 18/18*    (2006.01)
(52) U.S. Cl.
    USPC .................................. 606/46; 606/48; 606/50

(58) Field of Classification Search
    USPC .......................................... 606/50–52, 46, 48
    See application file for complete search history.

(56) References Cited

U.S. PATENT DOCUMENTS

| 6,679,882 B1 | 1/2004 | Kornerup |
| 2002/0022838 A1 | 2/2002 | Cunningham et al. |

(Continued)

FOREIGN PATENT DOCUMENTS

| EP | 1810621 A1 | 7/2007 |
| EP | 2548527 A1 | 1/2013 |

(Continued)

OTHER PUBLICATIONS

EP Office Action Dated May 13, 2013 for EP Application 11834369.8, pp. 1-7.

(Continued)

*Primary Examiner* — Linda Dvorak
*Assistant Examiner* — Jaymi Della
(74) *Attorney, Agent, or Firm* — Gael D. Tisack; Darryl Newell; MacMillan, Sobanski & Todd, LLC

(57) ABSTRACT

A surgical treatment device which is used together with an endoscope, includes a sheath, a treatment portion which is arranged at the distal end portion of the sheath and includes first to third electrodes configured to treat a living tissue by using electrical energy, an operation portion which is arranged at a proximal end portion of the sheath and which is configured to operate the treatment portion, and a switching portion which is configured to switch between a first mode in which a treatment is given by using the first electrode and at least one of the second and third electrodes in the treatment portion and a second mode in which a treatment is given by using the second and third electrodes.

14 Claims, 17 Drawing Sheets

(56) References Cited

U.S. PATENT DOCUMENTS

| | | |
|---|---|---|
| 2003/0130654 A1* | 7/2003 | Kasahara et al. ............... 606/45 |
| 2006/0211916 A1* | 9/2006 | Kasahara et al. ............. 600/114 |
| 2006/0235450 A1 | 10/2006 | Kasahara et al. |
| 2008/0015567 A1 | 1/2008 | Kimura |
| 2009/0024121 A1* | 1/2009 | Kasahara et al. ............... 606/39 |
| 2011/0230881 A1* | 9/2011 | Maeda et al. ................... 606/46 |

FOREIGN PATENT DOCUMENTS

| | | |
|---|---|---|
| JP | 6054801 A | 3/1994 |
| JP | 9122141 A | 5/1997 |
| JP | 2003290248 | 10/2003 |
| WO | WO03055402 A1 | 7/2003 |
| WO | 2006/051593 A1 | 5/2006 |
| WO | WO2011114602 A1 | 9/2011 |

OTHER PUBLICATIONS

First Official Office Action of JPO, corresponding application JP2012535528, Sep. 28, 2012.

PCT Notification of Transmittal of Translation of the International Preliminary Report on Patentability, pp. 1-6, May 10, 2013.

* cited by examiner

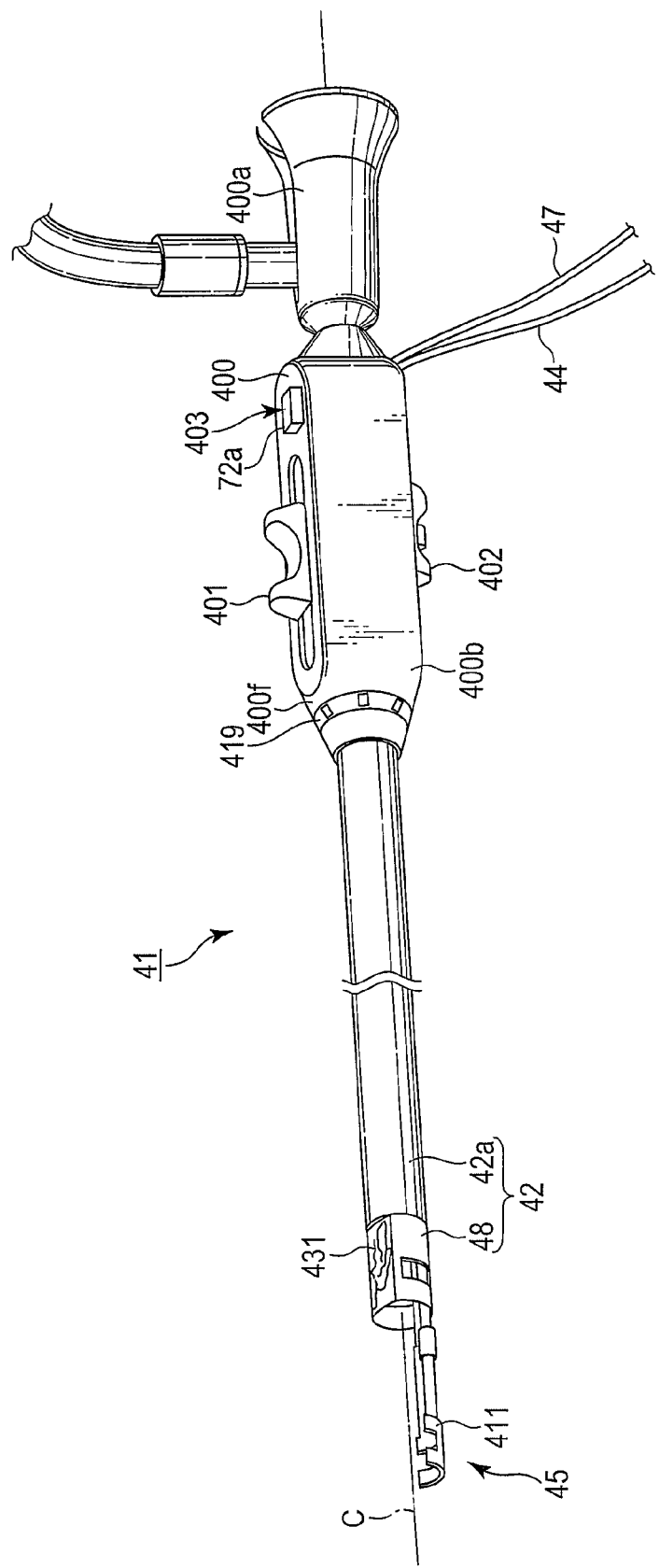
F I G. 2A

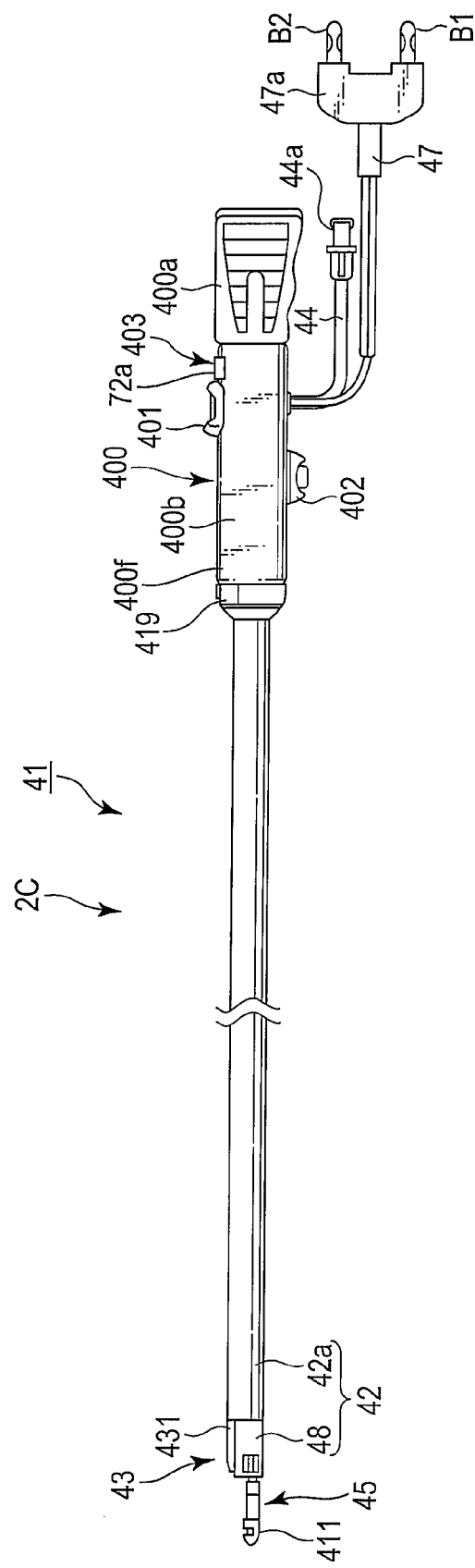
F I G. 2B

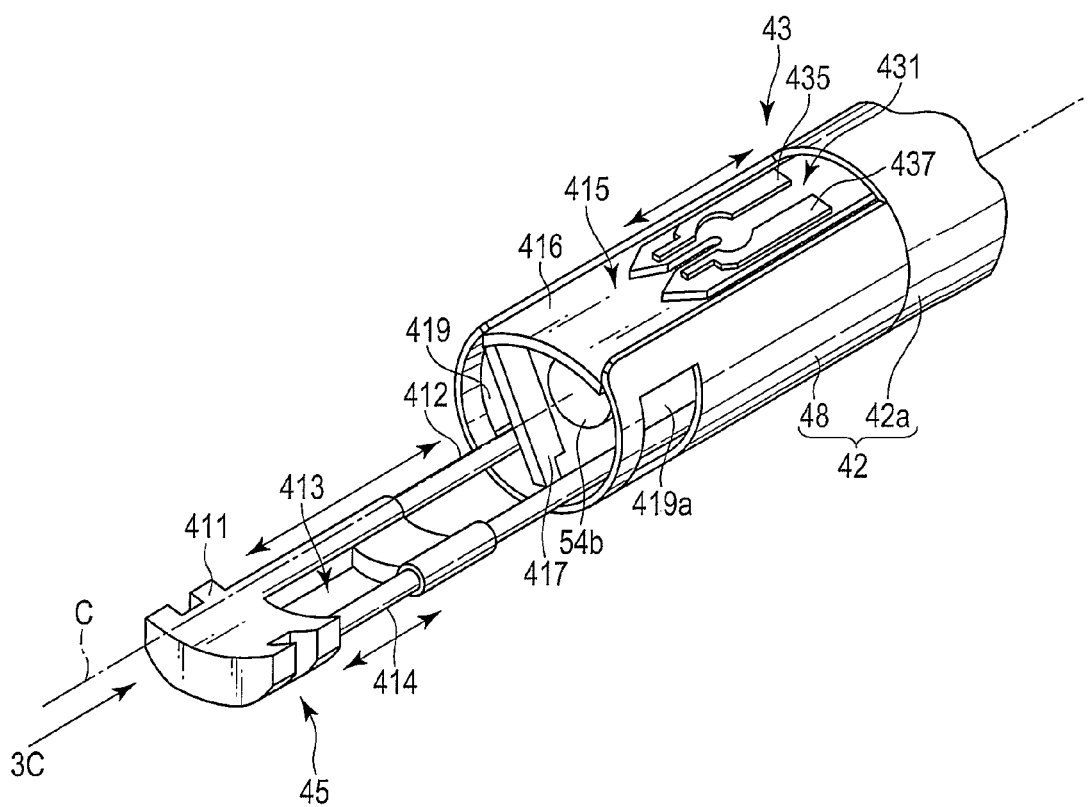
F I G. 3A

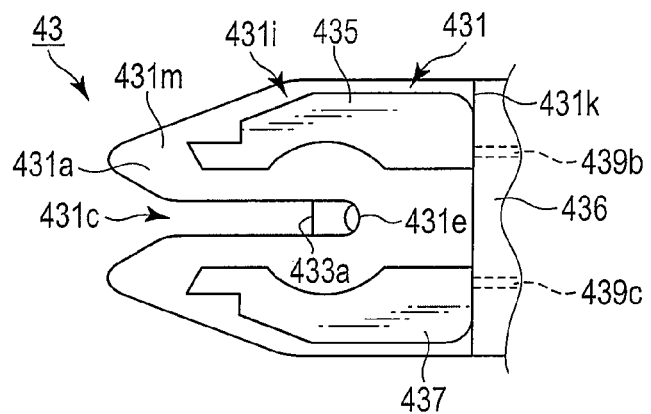
F I G. 5A
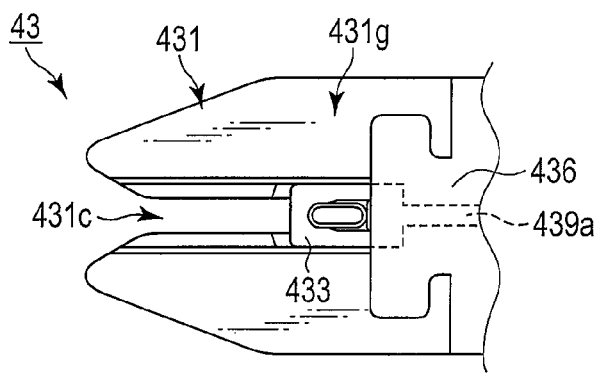
F I G. 5B
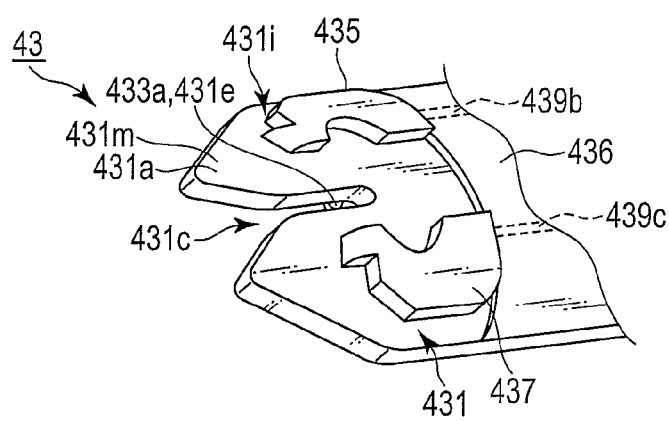
F I G. 5C

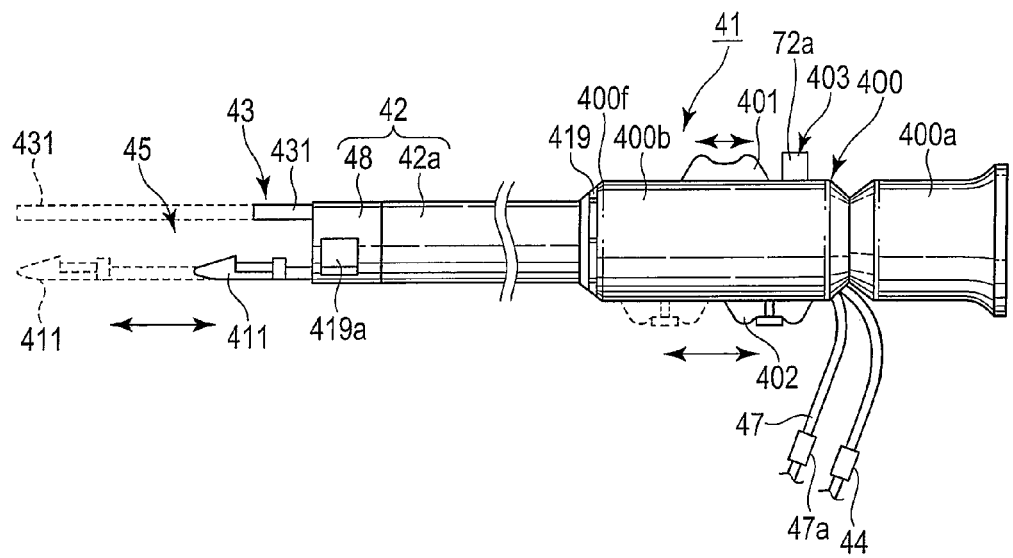
F I G. 7
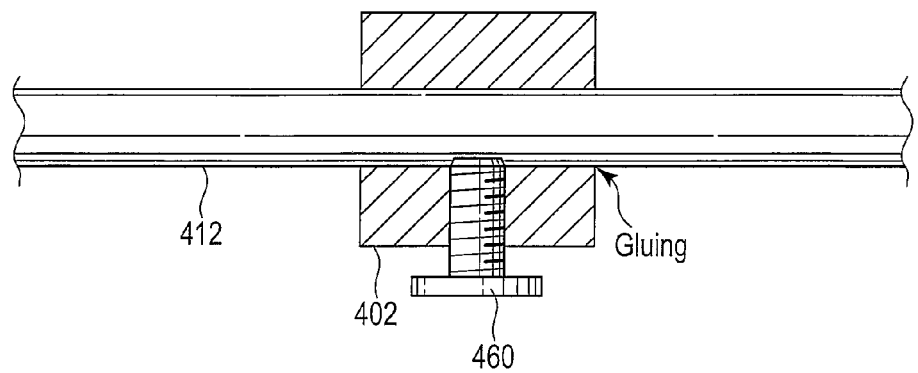
F I G. 8

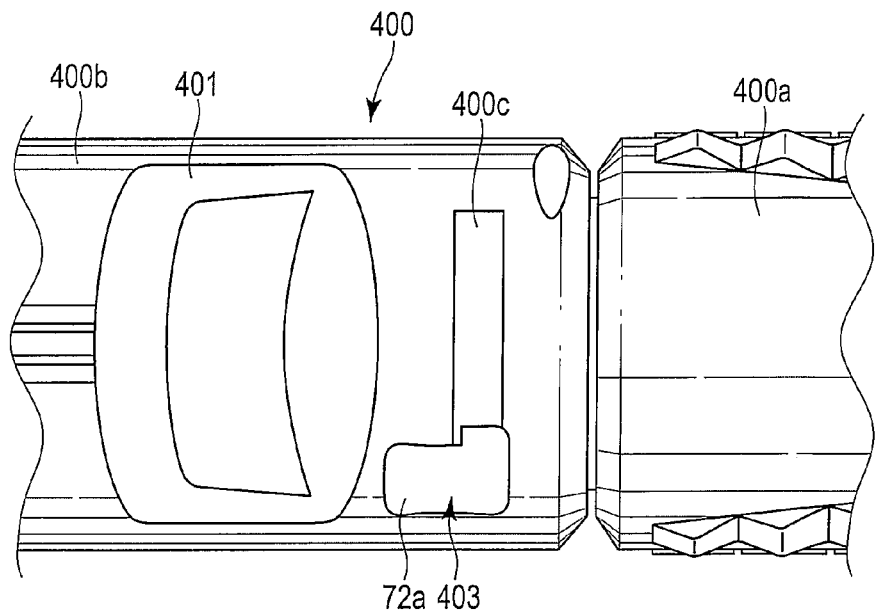
F I G. 9A
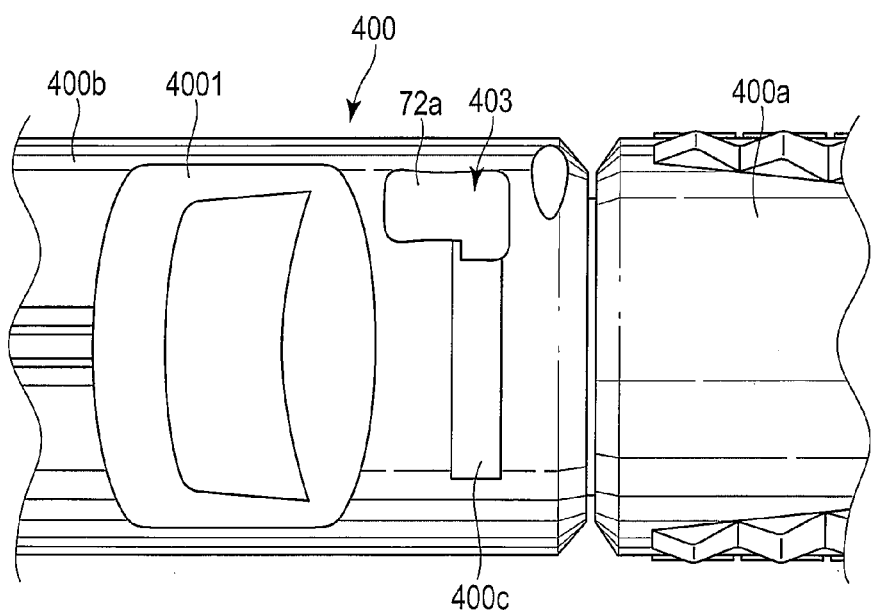
F I G. 9B

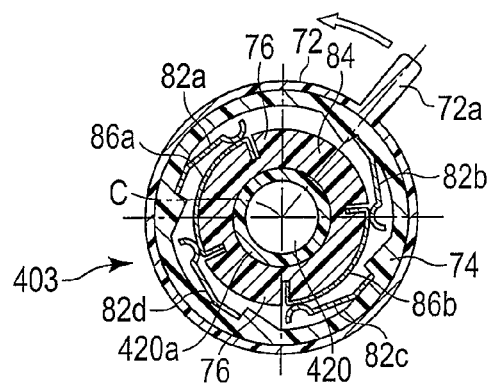
F I G. 10A
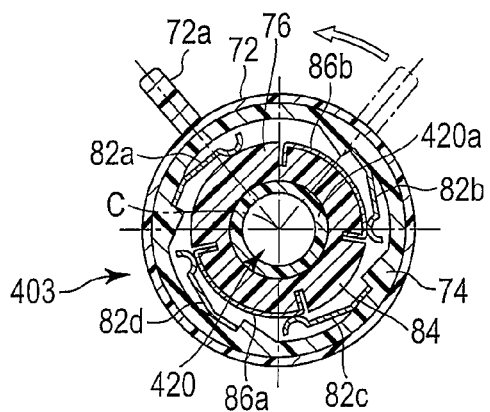
F I G. 10B
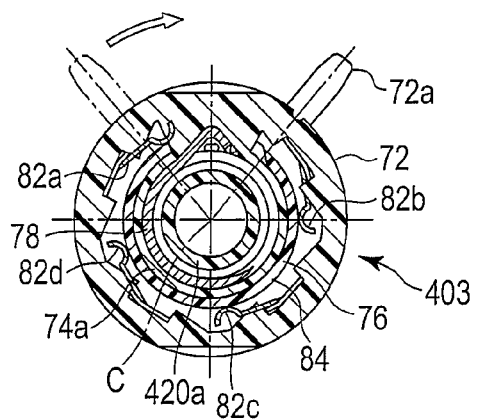
F I G. 10C

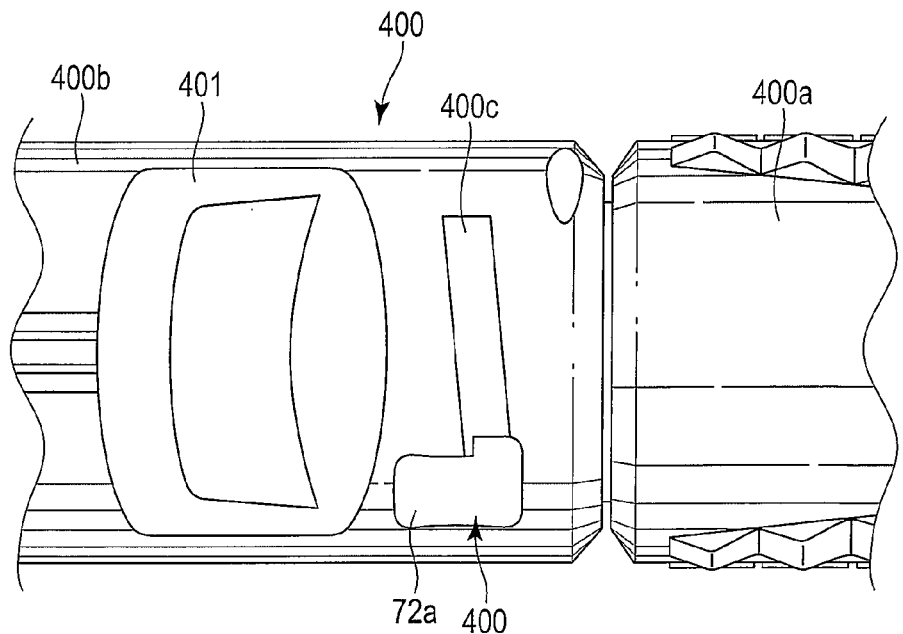
F I G. 11A
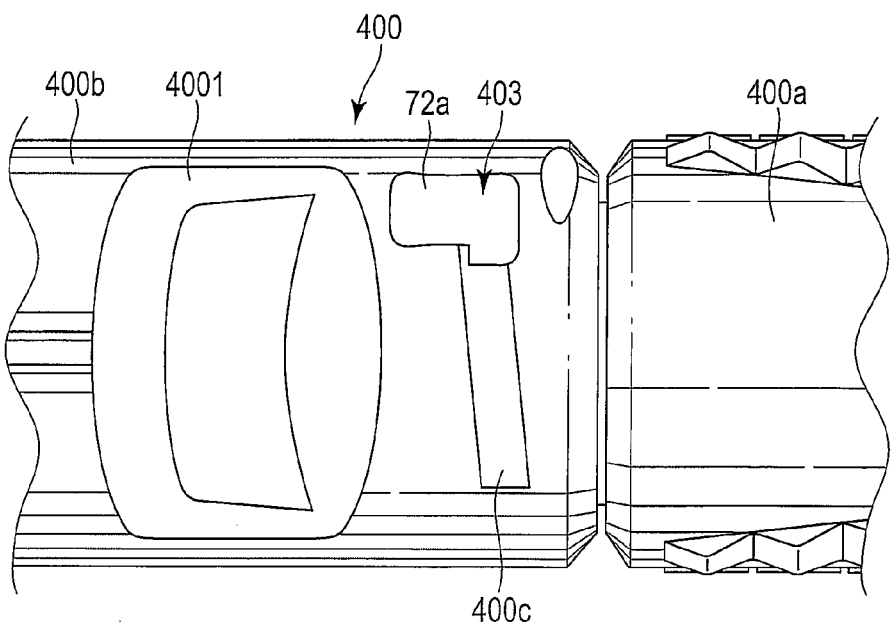
F I G. 11B

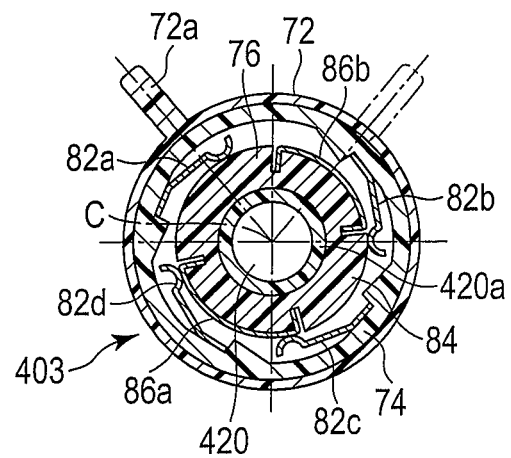
F I G. 12
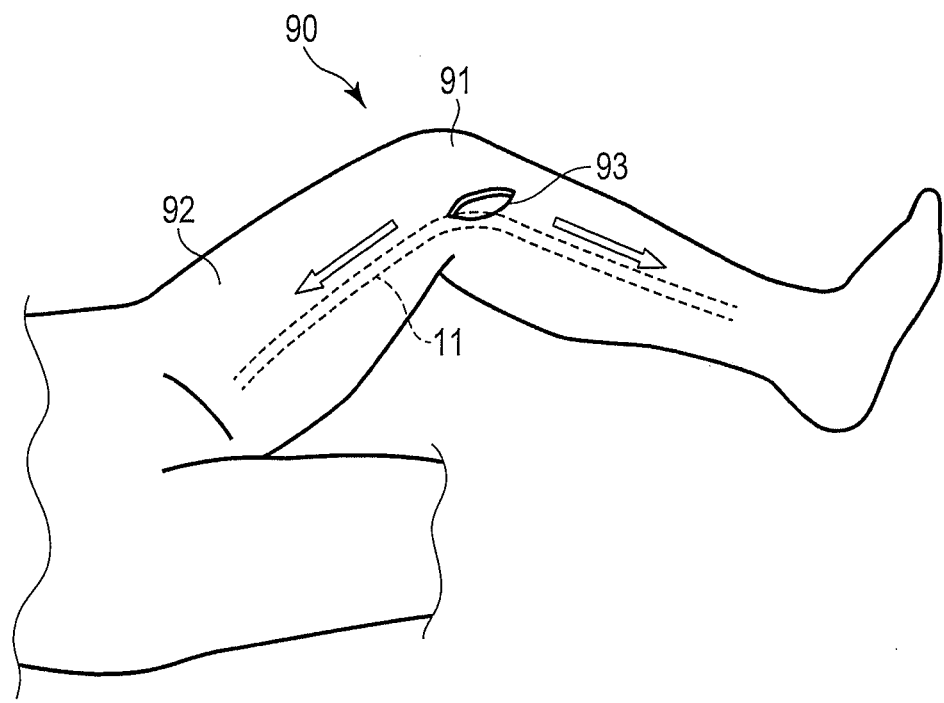
F I G. 13

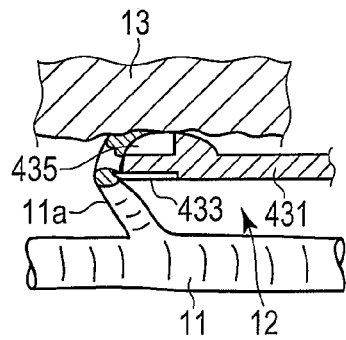
F I G. 15A
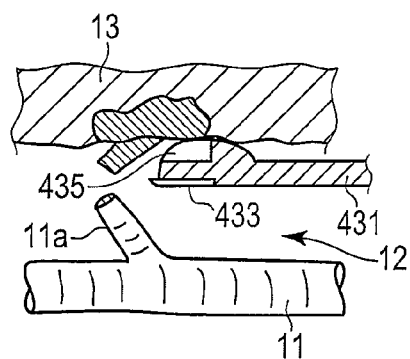
F I G. 15B
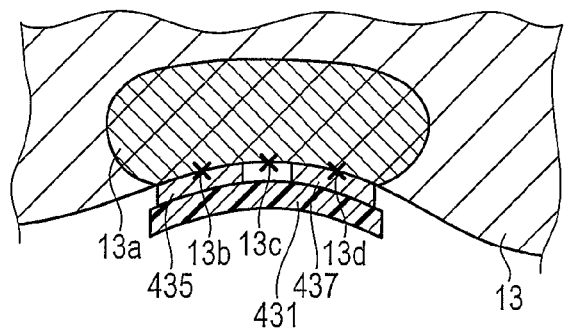
F I G. 16

US 8,702,700 B2

SURGICAL TREATMENT DEVICE

CROSS REFERENCE TO RELATED APPLICATIONS

This application is a Continuation Application of PCT Application No. PCT/JP2011/073991, filed Oct. 19, 2011 and based upon and claiming the benefit of priority from prior U.S. Provisional Application No. 61/394,802, filed Oct. 20, 2010, the entire contents of all of which are incorporated herein by reference.

BACKGROUND OF THE INVENTION

1. Field of the Invention

The present invention relates to a surgical treatment device configured to treat a living tissue such as a blood vessel.

2. Description of the Related Art

For example, U.S. Pat. No. 6,679,882 discloses a surgical treatment device in which a push button configured to change over an energization state when pressed along an axial direction of an insertion portion is arranged on a bent portion (a rear end) of a substantially-L-shaped handle. A living tissue can be coagulated by a pair of jaws when the push button is being released, and the living tissue can be incised by a plate shaped electric power application electrode when the push button is being pressed in the axial direction of the insertion portion.

BRIEF SUMMARY OF THE INVENTION

In an aspect of the present invention, a surgical treatment device which is used together with an endoscope, includes: a sheath; a treatment portion which is arranged at the distal end portion of the sheath and includes first to third electrodes configured to treat a living tissue by using electrical energy; an operation portion which is arranged at a proximal end portion of the sheath and which is configured to operate the treatment portion; and a switching portion which is configured to switch between a first mode in which a treatment is given by using the first electrode and at least one of the second and third electrodes in the treatment portion and a second mode in which a treatment is given by using the second and third electrodes.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2A is a perspective view of a harvester in the vessel harvesting system according to the embodiment;

FIG. 2B is a side view showing the harvester in the vessel harvesting system according to the embodiment;

FIG. 3A is an enlarged schematic perspective view showing a distal end portion and its periphery of an insertion portion of the harvester in the vessel harvesting system according to the embodiment;

FIG. 5A is a schematic plan view showing a cutter main body of a bipolar cutter of the harvester from a front surface side in the vessel harvesting system according to the embodiment;

FIG. 5B is a schematic plan view showing the cutter main body of the bipolar cutter of the harvester from a back surface side in the vessel harvesting system according to the embodiment;

FIG. 5C is a schematic perspective view showing the cutter main body of the bipolar cutter of the harvester from the front surface side in the vessel harvesting system according to the embodiment;

FIG. 7 is a schematic side view of the harvester in the vessel harvesting system according to the embodiment;

FIG. 8 is a schematic view showing a connection state of a vein keeper shaft and a vein keeper button of the harvester in the vessel harvesting system according to the embodiment;

FIG. 9A is a schematic plan view showing a state of a switching portion when the bipolar cutter of the harvester in the vessel harvesting system according to the embodiment is in the cutting mode;

FIG. 9B is a schematic plan view showing a state of the switching portion when the bipolar cutter of the harvester in the vessel harvesting system according to the embodiment is in the coagulation mode;

FIG. 10A is a schematic transverse cross-sectional view of the switching portion when the bipolar cutter of the harvester in the vessel harvesting system according to the embodiment is in the cutting mode;

FIG. 10B is a schematic transverse cross-sectional view of the switching portion when the bipolar cutter of the harvester in the vessel harvesting system according to the embodiment is in the coagulation mode;

FIG. 10C is a schematic transverse cross-sectional view showing a state that a coil spring is arranged between a support member and a drum of the switching portion when the bipolar cutter of the harvester in the vessel harvesting system according to the embodiment is in the cutting mode;

FIG. 11A is a schematic plan view showing a state of the switching portion when the bipolar cutter of the harvester in the vessel harvesting system according to a modification of the embodiment is in the cutting mode;

FIG. 11B is a schematic plan view showing a state of the switching portion when the bipolar cutter of the harvester in the vessel harvesting system according to the modification of the embodiment is in the coagulation mode;

FIG. 12 is a schematic transverse cross-sectional view when the bipolar cutter of the harvester in the vessel harvesting system according to the modification of the embodiment is in the coagulation mode;

FIG. 13 is a schematic view showing a blood vessel in a lower leg as a treatment target using the vessel harvesting system according to the embodiment;

FIG. 15A is a schematic longitudinal cross-sectional view showing a state that a cutting electrode of the bipolar cutter of the harvester in the vessel harvesting system according to the embodiment is brought into contact with a branch of a blood vessel and first and second coagulation electrodes are brought into contact with a vascular connective tissue;

FIG. 15B is a schematic longitudinal cross-sectional view showing a state that the branch of the blood vessel is cut by the cutting electrode of the bipolar cutter of the harvester in the vessel harvesting system according to the embodiment and the vascular connective tissue having the cut branch is coagulated by the first and second coagulation electrodes; and FIG. 16 is a schematic transverse cross-sectional view showing a state that the vascular connective tissue is coagulated by the first and second coagulated electrodes of the bipolar cutter of the harvester in the vessel harvesting system according to the embodiment.

DETAILED DESCRIPTION OF THE INVENTION

An embodiment according to the present invention will now be described hereinafter in detail with reference to FIG. 1 to FIG. 15B.

In the following embodiment, a subject (a living tissue including a sampling target tissue) is, e.g., a blood vessel 11 in a body cavity, a cut branch 11a of the blood vessel, or a bleeding point arranged on a wall portion in the body cavity. Further, a treatment includes incision, excision, perforation, detachment, coagulation, hemostasis, harvest, cautery, cutting, and others.

Figure 1:
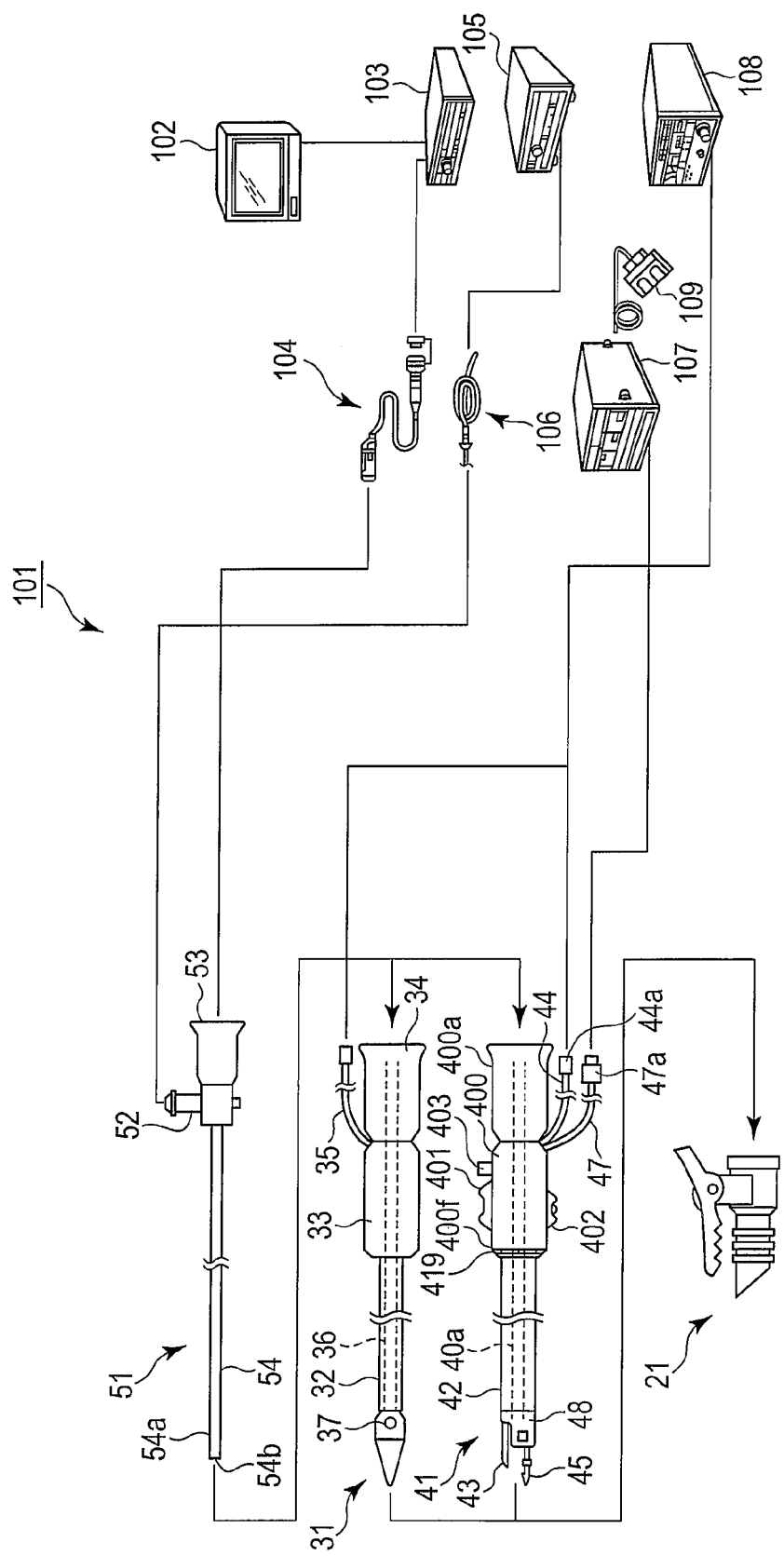
FIG. 1 is a schematic view showing a vessel harvesting system including an endoscope treatment device according to an embodiment.

FIG. 1 shows a vessel harvesting system (which will be simply referred to as a surgical system thereinafter) 101 including a later-described endoscope treatment device.

For example, in a Coronary Artery Bypass Grafting operation, a blood vessel as a subject is used for a bypass blood vessel. This blood vessel is, e.g., a great saphenous vein (which will be also simply referred to as a blood vessel hereinafter) from a femoral region to an ankle region in a lower leg as a sampling target blood vessel for a bypass or an artery in an upper-leg antebrachial region such as a radial artery. This blood vessel is sampled over the entire length by an endoscope treatment device or the like.

As shown in FIG. 1, the surgical system 101 includes a trocar 21, a dissector 31 which is a living tissue dissecting device (a surgical treatment device), a harvester 41 which is a living tissue cutting device (a surgical treatment device), and an endoscope 51 configured to observe a living tissue. Each of the dissector 31 and the harvester 41 can be inserted into the trocar 21, and the endoscope 51 is detachably held in each of the dissector 31 and the harvester 41. It is to be noted that a portion of the endoscope 51 inserted into each of the dissector 31 and the harvester 41 may be flexible or rigid, but being rigid is preferable. Here, an example of using a rigid endoscope will be explained.

As shown in FIG. 1, the surgical system 101 includes a trocar 21, a dissector 31 which is a living tissue dissecting device (a surgical treatment device), a harvester 41 which is a living tissue cutting device (a surgical treatment device), and a rigid endoscope 51 as the endoscope. Each of the dissector 31 and the harvester 41 can be inserted into the trocar 21, and the rigid endoscope 51 can be attached to each of the dissector 31 and the harvester 41.

The surgical system 101 further includes a video monitor 102 which is a display apparatus, a camera control unit (which will be referred to as a CCU hereinafter) connected to the video monitor 102, a video camera cable 104 connected to the CCU 103, a light source apparatus 105 which emits light, a light guide cable 106 which is connected to the light source apparatus 105, an electro-surgical generator 107 which flows a HF current to at least one of later-described electrodes 433, 436, and 437 of the harvester 41, and an insufflator 108 which supplies a desired gas such as a carbon dioxide gas. It is to be noted that a foot switch (a foot pedal) 109 having a pedal is disposed to the electro-surgical generator 107, a HF current flows through at least two of the later-described first to third application electrodes 433, 435, and 437 when the pedal is depressed with a foot, and supply of the HF current through the first to third electrodes 433, 435, and 437 is stopped when the pedal is released.

Since the rigid endoscope 51 can be inserted into the dissector 31 and the harvester 41, an operator harvests a blood vessel while watching an endoscopic image acquired by the rigid endoscope 51 in the video monitor 21. That is, each of the dissector 31 and the harvester 41 as the surgical treatment devices is used together with the rigid endoscope 51.

The rigid endoscope 51 will be described.

The rigid endoscope 51 includes a light guide connector portion 52, an eyepiece portion 53, and an insertion portion 54 having an outer case formed into a hard straight cylindrical shape by using a metal material such as a stainless steel material. The light guide connector portion 52 and the eyepiece portion 53 are arranged on a proximal end side of the insertion portion 54.

One end of the light guide cable 106 is connected to the light guide connector portion 52. The other end of the light guide cable 106 is connected to the light source apparatus 105. The light guide cable 106 is constituted of a light guide, e.g., an optical fiber. Light emitted from the light source apparatus 105 is supplied to the rigid endoscope 51 through the light guide cable 106. The rigid endoscope 51 illuminates the subject with this light from a distal end portion 54a of the insertion portion 54 which is a distal end portion of the rigid endoscope 51.

The video camera cable 104 is connected to the eyepiece portion 53 of the rigid endoscope 51. The video camera cable 104 is connected to the CCU 103, and the CCU 103 is connected to the video monitor 102. Further, an image of the subject acquired by the rigid endoscope 51 is displayed in the video monitor 102.

The insertion portion 54 of the rigid endoscope 51 is inserted into a later-described rigid scope insertion channel 36 of the dissector 31 from the proximal end side of the dissector 31. Furthermore, the insertion portion 54 is inserted into a rigid scope insertion channel 420 piercing through the later-described insertion portion 42 of the harvester 41 from the proximal end side of the harvester 41. It is to be noted that the eyepiece portion 53 of the rigid endoscope 51 is detachably fixed to each of later-described endoscope holding portions 34 and 400a.

The insertion portion 54 of the rigid endoscope 51 has an observation surface 54b (an objective lens) of a non-illustrated imaging system that images the subject at the distal end portion 54a thereof. An image of the subject acquired through the observation surface 54b is displayed in the video monitor 102 via the video camera cable 104 and the CCU 103 as described above.

The dissector 31 will now be described.

The dissector 31 has an insertion portion 32 which is inserted into a body cavity through the trocar 21, a grip portion 33, the endoscope holding portion 34, an air supply tube 35, and the rigid scope insertion channel 36 into which the insertion portion 54 of the rigid endoscope 51 is inserted.

The air supply tube 35 is connected to the insufflator 108 through a non-illustrated gas tube, and a desired gas is supplied. The gas is discharged from an opening portion 37 provided at a distal end portion of the insertion portion 32 of the dissector 31. The rigid scope insertion channel 36 is configured along an axial direction of the dissector 31 from the proximal end side of the dissector 31 to the distal end portion of the insertion portion 32 in the dissector 31. When the insertion portion 54 of the rigid endoscope 51 is inserted into the rigid scope insertion channel 36, the grip portion 33 can detachably hold the eyepiece portion 53 of the rigid endoscope 51. Therefore, the dissector 31 gives the subject a treatment with the rigid endoscope 51 being attached thereto.

The harvester 41 which is the surgical treatment device according to the embodiment will now be described with reference to FIG. 1 to FIG. 12.

Figure 2C:
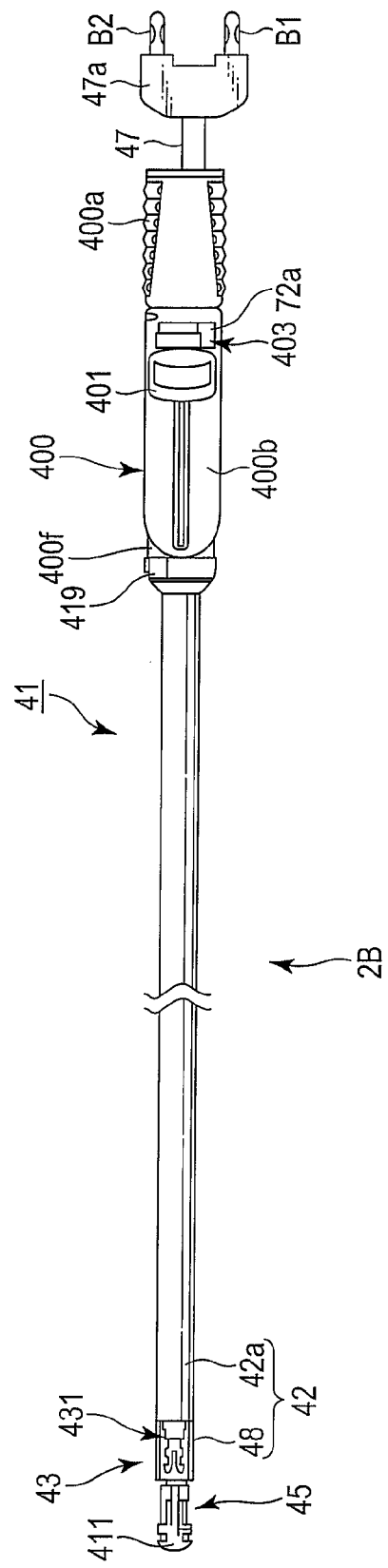
FIG. 2C is a top view of the harvester in the vessel harvesting system according to the embodiment as seen from a direction of an arrow 2C in FIG. 2B.

As shown in FIG. 1 to FIG. 2C, the harvester 41 includes a cylindrical insertion portion (a sheath) 42 which is inserted into a body cavity through the trocar 21, a substantially cylindrical operating portion 400 which is continuously provided at the proximal end of the insertion portion 42 and has a grip portion 400b gripped by an operator, and the substantially cylindrical endoscope holding portion (a scope holder) 400a arranged at a proximal end portion of the operating portion 400. The insertion portion 42, the operating portion 400, and the endoscope holding portion 400a have a longitudinal axis C which also serves as a common central axis. The insertion portion 42, the operating portion 400, and the endoscope holding portion 400a have the common central axis C. Moreover, the central axis C of the insertion portion 42, the operating portion 400, and the endoscope holding portion 400a is defined by the distal end portion and the proximal end portion of the insertion portion 42. It is to be noted that the insertion portion 42 and the operation portion 400 may have the coaxial central axis C or the parallel central axis C. That is, in any case, the central axis C of the insertion portion 42 and the operation portion 400 is parallel.

As shown in FIG. 2A to FIG. 3C, the insertion portion 42 includes an insertion portion main body 42a and a distal end cover 48. It is preferable that the insertion portion main body 42 is made of a metal material such as a stainless steel material in order to assure rigidity.

The distal end cover 48 at the distal end portion of the insertion portion 42 is made of, e.g., transparent plastic (e.g., polycarbonate or polysulfone). When the distal end cover 48 is made of plastic, an edge or the like at the distal end portion of the insertion portion 42 is improved. That is, the distal end cover 48 can prevent the edge from damaging the inside of a body cavity and improve insertability of the insertion portion 42 into the body cavity. Additionally, since the transparent material is used, when a later-described wiper 417 is operated in a situation that the inside of the distal end cover 48 is clogged with an attached matter 418, the attached matter 418 can be easily confirmed. It is to be noted that the rigidity of the entire insertion portion 42 can be assured by the insertion portion main body 42a.

Figure 3B:
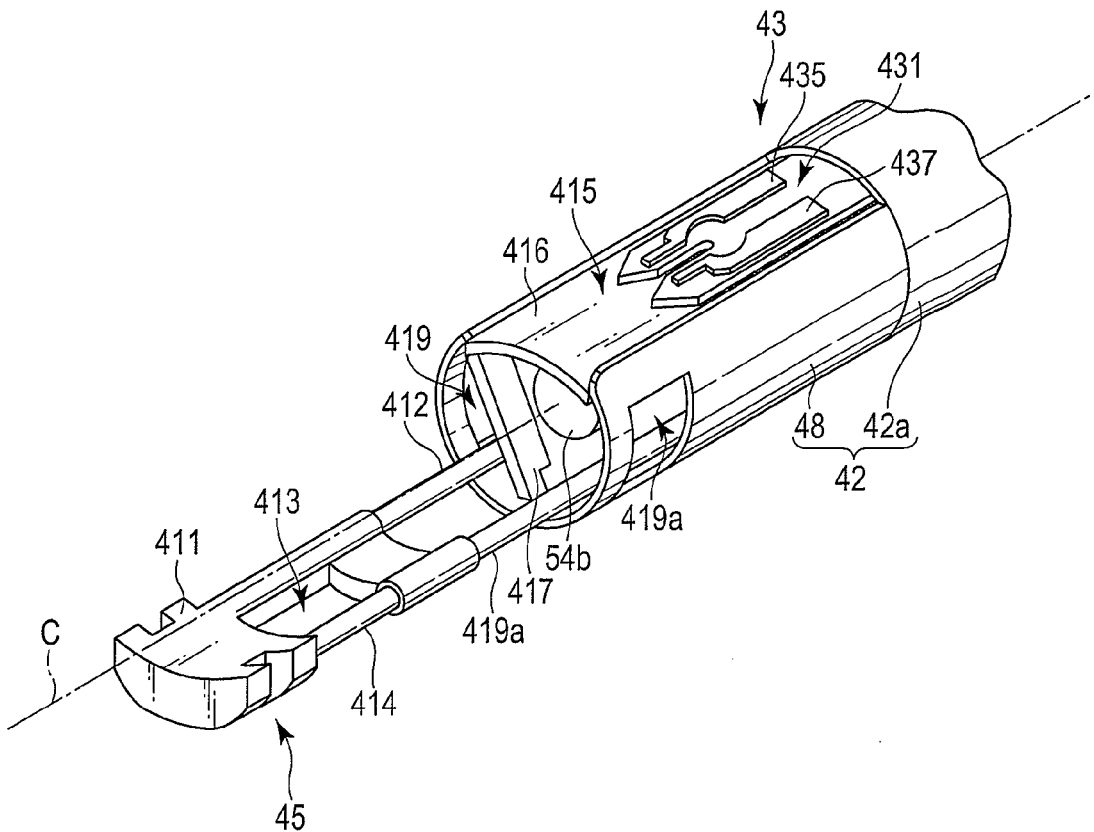
FIG. 3B is an enlarged schematic perspective view showing the distal end portion and its periphery of the insertion portion of the harvester in the vessel harvesting system according to the embodiment.

Additionally, as shown in FIG. 3A and FIG. 3B, a sweeping hole 419a from which the attached matter 418 (see FIG. 3C) wiped out by the wiper 417 is swept out is arranged in the cylindrical distal end cover 48. It is to be noted that, as the attached matter 418, for example, there is blood, fat, or smoke produced by a cautery knife. Further, in the wiper 417, the other end of the wiper 417 which is a distal end with respect to a proximal end to which a wiper shaft 500 is fixed may wipe off an inner peripheral surface of a later-described guard portion 416.

Figure 4A:
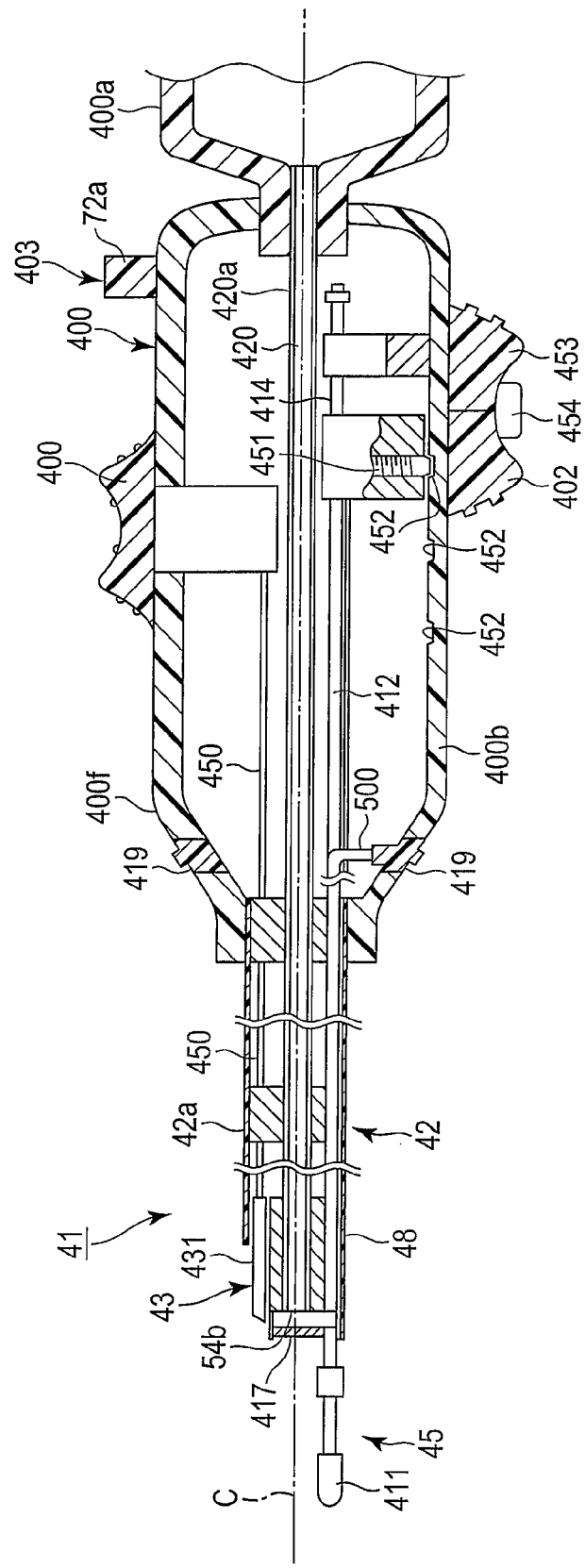
FIG. 4A is a schematic longitudinal cross-sectional view of the harvester in the vessel harvesting system according to the embodiment.

The endoscope holding portion 400a shown in FIG. 1 to FIG. 2C is used for easily and assuredly fixing the rigid endoscope 51 at the proximal end portion of the harvester 41 (the endoscope holding portion 400a). It is to be noted that, as shown in FIG. 1 and FIG. 4A, in the harvester 41, a metal tube member 420a that forms the rigid scope insertion channel 420 is inserted from the proximal end side of the operation portion 400 to the distal end part (the distal end cover 48) of the insertion portion 42 along the central axis C (the longitudinal axis direction) of the harvester 41.

Figure 3C:
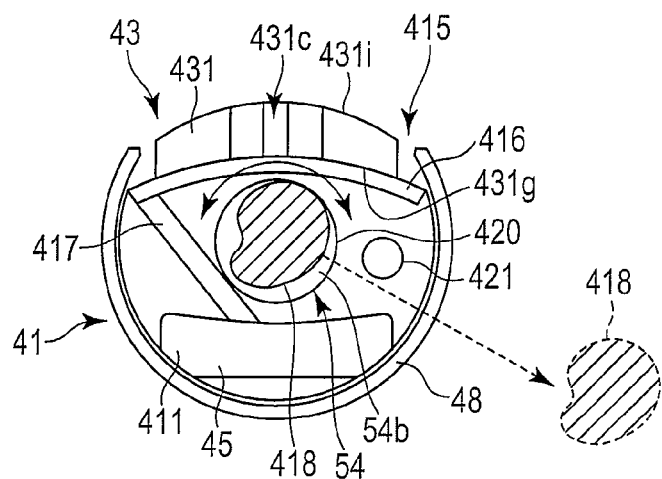
FIG. 3C is a schematic front view showing a state that the distal end portion of the insertion portion of the harvester in the vessel harvesting system according to the embodiment is observed from a direction of an arrow 3C in FIG. 3A.

As shown in FIG. 3C, on the desired inner side of the distal end surface of the insertion portion 42, an opening portion of the tube member 420a into which the rigid endoscope 51 is inserted and an opening portion of an air supply channel 421 through which air is supplied as will be described later are arranged to be adjacent to each other.

As shown in FIG. 3A to FIG. 4B, on an inner peripheral surface of the cylindrical insertion portion 42 of the harvester 41, a bipolar cutter (a medical appliance) 43 is arranged to be independently movable along the longitudinal axis direction (an axis direction of the central axis C) of the insertion portion 42. That is, the harvester 41 includes the bipolar cutter (the medical appliance) 43 in addition to the insertion portion (the sheath) 42, the operation portion 400 having the grip portion 400b, and the endoscope holding portion (the scope holder) 400a.

On the inner peripheral surface of the cylindrical insertion portion 42 of the harvester 41, a vein keeper 45 as a holder faces the bipolar cutter 43 in regard to the central axis C of the insertion portion 42, and it is arranged to be independently movable in the longitudinal axis direction (the axis direction of the central axis C) of the insertion portion 42. That is, the harvester 41 includes the vein keeper 45 in addition to the bipolar cutter 43.

As shown in FIG. 3A to FIG. 4B, on the inner peripheral surface of the cylindrical insertion portion 42, the bipolar cutter (the medical appliance) 43 and the vein keeper 45 which is the holder are arranged to face the central axis C of the insertion portion 42 and to be independently movable in the longitudinal axis direction (the axis direction of the central axis C) of the insertion portion 42. That is, the harvester 41 further includes the bipolar cutter 43 and the vein keeper 45.

The bipolar cutter 43 can move in the longitudinal axis direction of the insertion portion 42 by an operation of a later-described bipolar cutter button (a slider) 401 of the grip portion 400b of the operation portion 400, and the vein keeper 45 can move in the longitudinal axis direction of the insertion portion 42 by an operation of a later-described vein keeper button (a slider) 402 of the grip portion 400b of the operation portion 400.

Figure 4B:
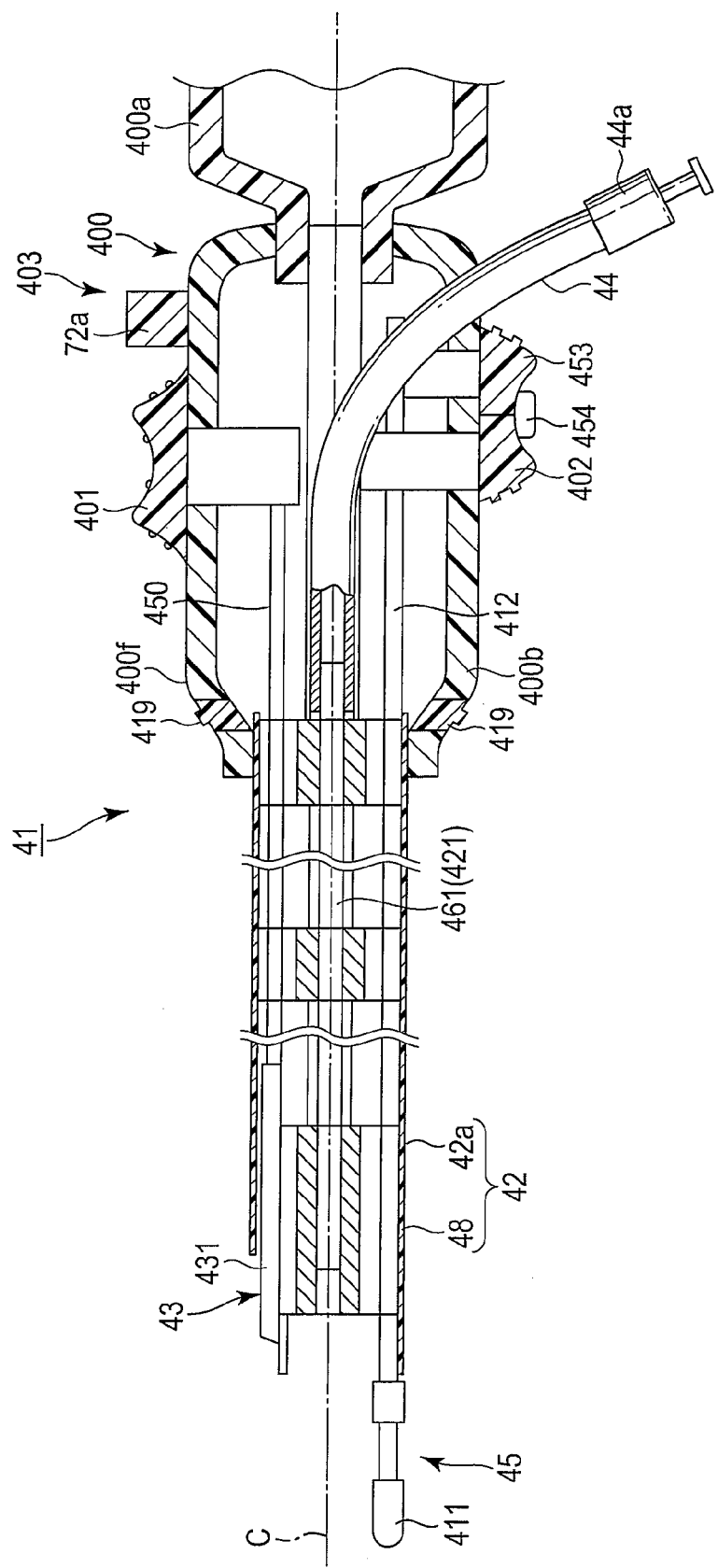
FIG. 4B is a schematic longitudinal cross-sectional view of the harvester in the vessel harvesting system according to the embodiment.

As shown in FIG. 3A and FIG. 3B, the vein keeper 45 includes a vein keeper shaft 412 which holds a substantially-U-shaped blood vessel holding base 411 to be retractable in the longitudinal direction of the insertion portion 42 and a lock shaft 414 which forms a closed space 413 for accommodating a blood vessel in the substantially-U-shaped blood vessel holding base 411 by moving forward or backward with respect to the blood vessel holding base 411 along the longitudinal direction of the insertion portion 42. As shown in FIG. 4A and FIG. 4B, the vein keeper shaft 412 and the lock shaft 414 are inserted into the insertion portion 42 and the operation portion 400.

As shown in FIG. 3A, the lock shaft 414 forms the closed space 413 when locked by the blood vessel holding base 411 like the vein keeper shaft 412. Furthermore, when the lock shaft 414 is unlocked, the lock shaft 414 releases the closed space 413 as shown in FIG. 3B, and it moves forward or backward in the longitudinal axis direction of the insertion portion 42 so that the blood vessel 11 can be accommodated in the closed space 413.

As shown in FIG. 3A and FIG. 3B, a notch 415 that is used for arranging a cutter main body 431 of the bipolar cutter 43 is formed in the distal end cover 48 of the insertion portion 42 of the harvester 41. Since the notch 415 is provided, later-described second and third application electrodes 435 and 437 enables coagulate a living tissue without protruding the cutter main body 431 toward the distal end side with respect to the distal end of the insertion portion 42 (the distal end of the distal end cover 48).

As shown in FIG. 3A and FIG. 3B, the bipolar cutter 43 includes the cutter main body 431 which is a treatment portion that treats the subject and a bipolar shaft 450 which is coupled with the cutter main body 431 and moves the cutter main body 431 forward and backward. The bipolar shaft 450 is interpolated into the insertion portion 42 through the notch 415 of the distal end cover 48, and it can move along the longitudinal axis direction of the insertion portion 42.

As shown in FIG. 3A to FIG. 3C, a guard portion 416 which has the cutter main body 431 arranged between itself and the inner peripheral surface of the insertion portion 42 and has a substantially-arc-like transverse cross section is arranged in the insertion portion 42. In a state that the cutter main body 431 faces the guard portion 416, a later-described coagulation can be given to a living tissue, but a cutting cannot be given. Therefore, in case of giving the cutting, the cutter main body 431 must be moved to the distal end side with respect to the distal end of the insertion portion 42. Moreover, the guard portion 416 protects the inside of the insertion portion 42 that is exposed by the notch 415, and it also prevents force from being applied to the cutter main body 431 toward the central axis C when guiding the cutter main body 431 toward a predetermined direction (the longitudinal axis direction of the insertion portion 42). It is to be noted that, in both a state that the coagulation is possible but the cutting is impossible and a state that both the coagulation and the cutting are possible, the cutter main body 431 is arranged at the distal end portion of the insertion portion 42.

As shown in FIG. 5A to FIG. 5C, the cutter main body 431 includes a first application electrode 433, a second application electrode 435, and a third application electrode 437.

The first application electrode 433 is mainly used for cutting a living tissue. The first application electrode 433 will be referred to as a cutting electrode hereinafter. As will be described later, the second and third application electrodes 435 and 437 are used as ground electrodes when cutting a living tissue which is in contact with the cutting electrode 433, and the second and third application electrodes 435 and 437 are used as coagulation electrodes for coagulating a contacting living tissue when coagulating the living tissue. The second application electrode 435 will be mainly referred to as a first coagulation electrode and the third application electrode 437 will be referred to as a second coagulation electrode hereinafter.

The cutting electrode 433 is roughly formed into a substantially rectangular flat plate. The first and second coagulation electrodes 435 and 437 have the same size (an outer surface area) and are symmetrically formed. An outer surface area of the cutting electrode 433 is formed to be sufficiently larger than an outer surface area of each of the first and second coagulation electrodes 435 and 437.

Figure 6A:
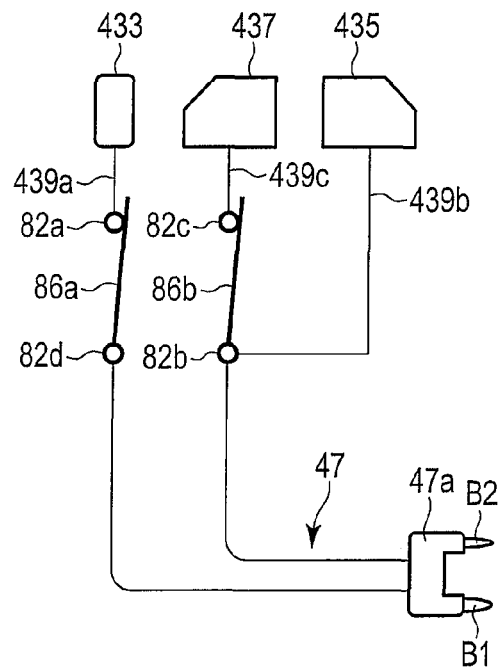
FIG. 6A is a schematic circuit diagram when the bipolar cutter of the harvester in the vessel harvesting system according to the embodiment is in a cutting mode.
Figure 6B:
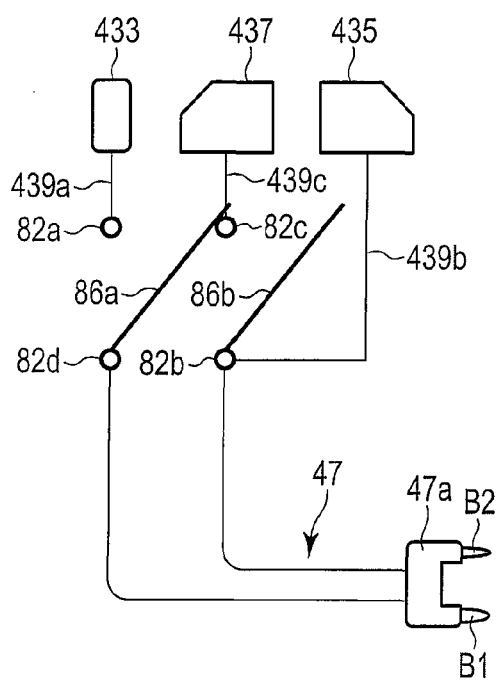
FIG. 6B is a schematic circuit diagram when the bipolar cutter of the harvester in the vessel harvesting system according to the embodiment is in a coagulation mode.

Additionally, a first lead wire 439a is connected to the cutting electrode 433, a second lead wire 439b is connected to the first coagulation electrode 435, and a third lead wire 439c is connected to the second coagulation electrode 437. It is to be noted that, as shown in FIG. 6A and FIG. 6B, the first lead wire 439a is connected to a later-described first spring contact 82a, the second lead wire 439b is connected to a later-described second spring contact 82b, and the third lead wire 439c is connected to a later-described third spring contact 82c.

The cutter main body 431 may be made of a synthetic resin which is a transparent insulating member of, e.g., polycarbonate, or it may be formed of a heat resisting member having insulation properties. When the cutter main body 431 is formed of the heat resisting member having the insulation properties, it is more particularly formed by using a material, e.g., zirconia ceramics (zirconium oxide) or alumina (aluminum oxide) which is a ceramic constructional material having high heat resistance.

The cutter main body 431 includes a V-shaped groove 431c as a guide portion which is formed at the distal end 431a of the cutter main body 431 and guides the subject to the cutting electrode 433 when the cutter main body 431 moves toward the subject such as a branch 11a. That is, the distal end 431a of the cutter main body 431 is bifurcated, and the V-shaped groove 431c is formed at the center of the bifurcation. It is to be noted, it is preferable that the cuter main body 431 is formed into a curved shape, e.g., a shape parallel the inner peripheral surface of the insertion portion 42 to assure a region of the tube member 420a in which the insertion section 54 of the rigid endoscope 51 is arranged and facilitate contact of a surface of the cutter main body 431 (a surface apart from the vein keeper 45) with the living tissue.

The cutting electrode 433 is arranged while being fixed on a back side (a surface which faces the vein keeper 45 in proximity thereto) 431g which is a first surface of the cutter main body 431 so that a contact portion 433a of the cutting electrode 433 can be exposed on a bottom surface 431e of the V-shaped groove 431c in the longitudinal direction of the cutter main body 431. That is, the cutting electrode 433 faces the guard portion 416 (see FIG. 3A to FIG. 3C) formed at the distal end portion of the insertion portion 42.

The first coagulation electrode 435 and the second coagulation electrode 437 are arranged on a surface different from the back side 431g (a surface apart from the guard portion 416 and the vein keeper 45). That is, the first and second coagulation electrodes 435 and 437 are fixed to a surface 431i which is a second surface.

The first and second coagulation electrodes 435 and 437 are arranged from a proximal end 431k to a distal end 431m of the surface 431i in the longitudinal direction of the cutter main body 431 on the surface 431*i* in such a manner that they can produce a symmetric appearance with the V-shaped groove 431*c* at the center along the longitudinal axis direction of the cutter main body 431 (the longitudinal axis direction of the insertion portion 45).

Furthermore, the cutting electrode 433, the first coagulation electrode 435, and the second coagulation electrode 437 themselves are electrically insulated different bodies in the embodiment. Proximal end parts of the cutting electrode 433 and the first and second coagulation electrodes 435 and 437 are covered with an insulating member 436.

The operation portion 400 will now be described with reference to FIG. 1 to FIG. 2C, FIG. 4A, FIG. 4B, and FIG. 7 to FIG. 12.

As shown in FIG. 1 to FIG. 2C and FIG. 7, an electrical cable 47 for the bipolar cutter 43 and an air supply tube 44 are arranged with respect to the operation portion 400. As shown in FIG. 2B, FIG. 2C, and FIG. 6A to FIG. 7, a bipolar connector (a bipolar plug) 47*a* connected with the electro-surgical generator 107 is fixed at a proximal end of the electrical cable 47. The bipolar connector 47*a* includes two pins B1 and B2 that define polarities of the first to third application electrodes 433, 435, and 437 of the bipolar cutter 43 when connected to the electro-surgical generator 107. In addition, it is preferable for the pins B1 and B2 to have different lengths or shapes so that the polarities of the first to third application electrodes 433, 435, and 437 of the bipolar cutter 43 can be easily recognized or to be identifiable by, e.g., color coding even though the pins B1 and B2 have the same size or the same shape. In this case, the bipolar connector 47*a* is connected to the electro-surgical generator 107 in a predetermined state.

As shown in FIG. 4B, an air supply connector 44*a* is arranged at a proximal end of the air supply tube 44. The air supply connector 44*a* is connected to the insufflator 108 through a non-illustrated gas tube. At this moment, a desired gas is supplied to the air supply tube 44 from the insufflator 108 through the non-illustrated gas tube. The desired gas is, e.g., a carbon dioxide gas as described above. Further, in the operation portion 400, one end of an air supply pipe 461 is fitted in the air supply tube 44. As shown in FIG. 4B, in the harvester 41, the air supply pipe 461 is inserted from the proximal end side of the operation portion 400 to the distal end cover 48 at the distal end portion of the insertion portion 42 along the axial direction of the harvester 41. The air supply pipe 461 is made of a metal that forms the air supply channel 421. The desired gas supplied from the insufflator 108 is discharged from the opening portion of the air supply channel 421 through the air supply tube 44 and the air supply pipe 461.

As shown in FIG. 2A to FIG. 2C, FIG. 4A, FIG. 4B, and FIG. 7, the bipolar cutter button (a moving member) 401 that can move forward and backward in the longitudinal axis direction of the grip portion 400*b* to operate the bipolar cutter 43, the vein keeper button (a moving member) 402 that can move forward and backward in the longitudinal axis direction of the grip portion 400*b* to operate the vein keeper 45, and a wiper operation ring 419 that can rotationally move about the central axis C to operate the wiper 417 are arranged on the grip portion 400*b* of the operation portion 400. Here, the bipolar cutter button 401 and the vein keeper button 402 are placed to face each other like the arrangement of the bipolar cutter 43 and the vein keeper 45 in the insertion portion 42. The wiper operation ring 419 is arranged on the entire circumference of a distal end part 400*f* of the operation portion 400 (the grip portion 400*b*) on the distal end side of the bipolar cutter button 401 and the vein keeper button 402.

As shown in FIG. 4A and FIG. 4B, the bipolar shaft 450 which is inserted into the insertion portion 42 and the grip portion 400*b* and coupled with the bipolar cutter 43 is connected with the bipolar cutter button 401. That is, the bipolar cutter 43 is coupled with the bipolar cutter button 401 through the bipolar shaft 450 which is inserted into the insertion portion 42.

When the bipolar cutter button 401 moves forward or backward in the longitudinal direction of the grip portion 400*b* in the operation portion 400, the bipolar cutter 43 moves forward or backward with respect to the distal end of the insertion portion 42 through the bipolar shaft 450 in cooperation with this forward or backward movement. In other words, when the bipolar cutter button 401 moves forward or backward along the longitudinal axis direction of the grip portion 400*b*, this forward/backward moving force is transmitted to the bipolar cutter 43 through the bipolar shaft 450, and the bipolar cutter 43 moves forward or backward in the longitudinal axis direction.

As shown in FIG. 4A and FIG. 4B, the vein keeper shaft 412 which is inserted into the insertion portion 42 and the grip portion 400*b* and coupled with the vein keeper 45 is connected with the vein keeper button 402. That is, the vein keeper 45 is coupled with the vein keeper button 402 through the vein keeper shaft 412 inserted into the insertion portion 42.

When the vein keeper button 402 moves forward or backward in the longitudinal axis direction of the grip portion 400*b*, the vein keeper 45 moves forward or backward through the vein keeper shaft 412 in cooperation with this forward or backward movement. In other words, when the vein keeper button 402 moves forward or backward along the longitudinal axis direction of the grip portion 400*b*, this forward/backward moving force is transmitted to the vein keeper 45 through the vein keeper shaft 412, and the vein keeper 45 moves forward or backward with respect to the distal end of the insertion portion 42.

It is to be noted that, as shown in FIG. 4A, a click mechanism 451 which holds the vein keeper button 402 and the vein keeper shaft 412 and fixes positions of the vein keeper button 402 and the vein keeper shaft 412 is arranged on the inner surface (the inside) of the grip portion 400*b*. For example, three click grooves 452 are formed on the inner peripheral surface of the grip portion 400*b*. The click mechanism 451 is energized toward the click grooves 452.

The click mechanism 451 moves on the inner peripheral surface of the grip portion 400*b* in cooperation with the integral movement of the vein keeper button 402 and the vein keeper shaft 412. In this situation, the click mechanism 451 is placed in, e.g., any one of the three click grooves 452 provided on the inner surface of the grip portion 400*b* and pin-pushes the inner surface (the click groove 452) of the grip portion 400*b*. Then, the vein keeper button 402 and the vein keeper shaft 412 are stably fixed at this position, by the click mechanism 451 that pin-pushes the click groove 452.

It is to be noted that, when force acts on the vein keeper button 402 in the longitudinal axis direction of the grip portion 400*b*, the click mechanism 451 easily moves out from the click groove 452.

As shown in FIG. 4A and FIG. 4B, a lock button 453 which is detachably coupled with the vein keeper button 402 and a lock button 454 which is pressed down to separate the vein keeper button 402 from the lock button 453 are arranged on the grip portion 400*b*.

This lock button 453 is coupled with the lock shaft 414. When the lock button 453 moves forward or backward while being separated from the vein keeper button 402, the lock shaft 414 moves forward or backward as shown in FIG. 3A and FIG. 3B, and the blood vessel 11 can be accommodated in the closed space 413.

It is to be noted that the vein keeper button 402 is firmly fixed to the vein keeper shaft 412 by a screw 460 and adhesion as shown in FIG. 8.

As shown in FIG. 4A, the wiper operation ring 419 is coupled with the wiper shaft 500. The wiper shaft 500 is a rod-like shaft member which is inserted into the insertion portion 42 and coupled with the wiper 417. The wiper 417 is a wiping portion which is provided on the inner surface (the inside) of the insertion portion 42 on the distal end side and wipes out the attached matter 418 that has attached to the observation surface 54*b* arranged on the distal end portion 54*a* of the rigid endoscope 51 when rotationally moved by the wiper shaft 500.

As shown in FIG. 9A and FIG. 9B, in the substantially cylindrical operation portion 400, a switching portion (a switching module) 403 is provided at a position close to the endoscope holding portion 400*a* (a position on the rear end side of the grip portion 400*b*). The switching portion 403 is a revolving type switch configured to switch a treatment mode of the bipolar cutter 43 from a cutting mode (a first mode) to a coagulation mode (a second mode), and from the coagulation mode (the second mode) to the cutting mode (the first mode). FIG. 9A shows a state in the cutting mode, and FIG. 9B shows a state in the coagulation mode. The switching portion 403 is arranged between the inner peripheral surface of the cylindrical operation portion 400 and the outer peripheral surface of the tube member 420*a* forming the rigid scope insertion channel 420, and a later-described lever 72*a* protrudes from the outer peripheral surface through the opening 400*c* of the operation portion 400. It is to be noted that the opening 400*c* is formed on the rear end side of the bipolar cutter button 401 at a position close to the endoscope holding portion 400*a* (a position on the rear end side of the grip portion 400*b*).

As shown in FIG. 10A to FIG. 100, the switching portion 403 includes a substantially cylindrical revolving member 72 having the lever 72*a*, a substantially cylindrical support member 74 fixed to the operation portion 400, a drum 76 slidably arranged on the outer peripheral surface of the tube member 420*a*, and a coil spring (an energizing member) 78 which couples the support member 74 with the drum 76. It is to be noted that the revolving member 72 and the drum 76 are integrally formed. The revolving member 72, the support member 74, and the drum 76 are placed on a concentric position. As shown in FIG. 10A and FIG. 10B, in a transverse cross-sectional surface including the lever 72*a* of the switching portion 403, the support member 74 is arranged on the inner side of the revolving member 72, and the drum 76 is arranged on the inner side of the support member 74.

A position at which the support member 74 of the switching portion 403 is fixed to the operation portion 400 may be one or both the distal end part and the proximal end part of the support member 74, and the support member 74 is fixed to the operating portion 400 through, e.g., adhesion or screwing. Thus, the support member 74 does not move in both the axial direction of the central axis C and the circumferential direction with respect to the operation portion 400.

The lever 72*a* is formed to protrude outward from the outer peripheral surface of the substantially cylindrical revolving member 72. Moreover, the revolving member 72 slides about the central axis C of the harvester 41 and in the circumferential direction orthogonal to the central axis C with respect to the outer peripheral surface of the support member 74. Therefore, the lever 72*a* can be moved in the direction orthogonal to the central axis C of the operation portion 400 and the tube member 420*a*.

It is to be noted that, when moving the lever 72*a*, i.e., the revolving member 72 with respect to the support member 74, the movement of the revolving member 72 is not restricted to the direction orthogonal to the central axis C of the operation portion 400 and the tube member 420*a*, and the revolving member 72 may be movable in, e.g., an oblique direction along which a part of the spiral is formed with respect to the support member 74 as shown in FIG. 11A and FIG. 11B. That is, the direction along which the revolving member 72 is moved with respect to the support member 74 is not restricted to the direction orthogonal to the axial direction of the tube member 420*a*, and it may be the oblique direction. Therefore, the moving direction of the lever 72*a* is not only the direction orthogonal to the central axis C of the operation portion 400 and the tube member 420*a* but also a direction deviating from the direction parallel to the central axis C.

As shown in FIG. 10C, the coil spring 78 couples the support member 74 with the drum 76 at a position on the distal side of the lever 72*a*. The support member 74 includes an annular portion 74*a* which supports the outer periphery of the coil spring 78. One end of the coil spring 78 is fixed to the support member 74, and the other end of the coil spring 78 is not shown but fixed to the drum 76. In this embodiment, the coil spring 78 energizes the drum 76 and the revolving member 72 to a position shown in FIG. 9A (a position in a cutting mode) with respect to the support member 74. That is, the lever 72*a* of the switching portion 403 is energized by the coil spring 78 to stay at the position in FIG. 9A. To move the lever 72*a* of the switching portion 403, i.e., to switch from the cutting mode to the coagulation mode, switching is carried out by rotationally moving the switching portion 403 from the position depicted in FIG. 9A to the position shown in FIG. 9B against spring force of the coil spring 78. It is to be noted that, when a finger that holds the switching portion 403 at the position depicted in FIG. 9B is released, the switching portion 403 is restored to the position depicted in FIG. 9A by spring urging force of the coil spring 78.

As shown in FIG. 10A and FIG. 10B, for example, first to fourth spring contacts (electrical segments) 82*a*, 82*b*, 82*c*, and 82*d* are arranged on the support member 74 toward the drum 76. On the drum 76, a drum main body 84 having insulation properties and first and second drum-side contact (electrical segments) 86*a* and 86*b* arranged on the outer peripheral surface of the drum main body 84 are arranged. The first and second drum-side contacts 86*a* and 86*b* of the drum 76 are formed to face each other, for example.

As shown in FIG. 6A and FIG. 6B, the first contact 82*a* of the support member 74 is electrically connected to the cutting electrode 433 through the first lead wire 439*a*. The second contact 82*b* of the support member 74 is electrically connected to the pin B2 of the bipolar connector 47*a* through the electrical cable 47 and also electrically connected to the first coagulation electrode 435. The third contact 82*c* of the support member 74 is electrically connected to the second coagulation electrode 437. The fourth contact 82*d* of the support member 74 is electrically connected to the pin B1 of the bipolar connector 47*a* through the electrical cable 47.

When the lever 72*a* of the switching portion 403 is at the position of the cutting mode, as shown in FIG. 6A and FIG. 10A, the first contact 82*a* of the support member 74 is electrically connected to the fourth contact 82*d* of the support member 74 by the first drum-side contact 86*a*, and the second contact 82*b* of the support member 74 is electrically connected to the third contact 82*c* of the support member 74 by the second drum-side contact 86b. Thus, as shown in FIG. 6A, the pin B1 of the bipolar connector 47a is electrically connected to the cutting electrode 433, and the pin B2 of the bipolar connector 47a is electrically connected to the first and second coagulation electrodes 435 and 437. Therefore, the first and second coagulation electrodes 435 and 437 function as if they are one electrode.

When the lever 72a of the switching portion 403 is at the position of the coagulation mode, as shown in FIG. 6B and FIG. 10B, the third contact 82c of the support member 74 is electrically connected to the fourth contact 82d of the support member 74 by the first drum-side contact 86a. The first contact point 82a of the support member 74 is in contact with the drum main body 84 of the drum 76. It is to be noted that the second contact 82b of the support member 74 is in contact with the second drum-side contact 86b of the drum 76 in FIG. 10B, but the second contact 82b may be in contact with the drum main body 84 of the drum 76. Therefore, as shown in FIG. 6B, the pin B1 of the bipolar connector 47a is electrically connected to the second coagulation electrode 437, and the pin B2 of the bipolar connector 47a is electrically connected to the first coagulation electrode 435.

That is, the drum-side contact 86a comes into contact with the electrical contacts 82a and 82d arranged on the support member 74 of the operation portion 400 and the drum-side contact point 86b comes into contact with the electrical contacts 82b and 82c when the cutting mode shown in FIG. 6A and FIG. 10A is selected. And the drum-side contact point 86a comes into contact with the electrical contacts 82c and 82d arranged on the support member 74 of the operation portion 400 and the drum-side contact 86b comes into contact with the electrical contact 82b when the coagulation mode shown in FIG. 6B and FIG. 10B is selected.

It is to be noted that, even when the lever 72a is operated, a high-frequency current (electrical energy) does not flow through the electrodes 433, 435, and 437 from the electrosurgical generator 107 without depressing the pedal of the foot switch 109 by a foot, and an electrical treatment such as a cutting or coagulation of a living tissue is not given.

Additionally, since the first to fourth spring contacts 82a, 82b, 82c, and 82d have spring properties, when the first to fourth spring contacts 82a, 82b, 82c, and 82d are in contact with the drum main body 84 or the drum-side contact 86a and 86b, appropriate pressing force can be given in the direction of the central axis C of the drum main body 84. That is, a conductive state and an insulated state of the first to fourth spring contacts 82a, 82b, 82c, and 82d and the drum-side contacts 86a and 86b can be assuredly switched. Further, when the drum 76 rotationally moves with respect to the support member 74, the first to fourth spring contacts 82a, 82b, 82c, and 82d slide with respect to either the drum main body 84 or the contacts 86a and 86b, but large force can be prevented from being applied to the first to fourth spring contacts 82a, 82b, 82c, and 82d.

An operating method of the harvester 41 of the vessel harvesting system 101 according to this embodiment will now be described.

FIG. 13 shows a lower leg 90 of a patient, and reference numeral 11 denotes a blood vessel. First, when extracting the blood vessel 11 between a knee 91 and a groin 92, a skin incised portion 93 is provided at one position of the knee 91 immediately above the blood vessel 11 by using, e.g., a surgical knife.

In the skin incised portion 93, the blood vessel 11 is exposed by the dissector 31. Further, a tissue immediately above the blood vessel 11 is detached by the same dissector 31 at a distance that enables observation with naked eyes from the skin incised portion 93.

Subsequently, the dissector 31 is inserted into the trocar 21, the dissector 31 is slightly inserted along the blood vessel 11 from the skin incised portion 93, then the trocar 21 is inserted obliquely (in substantially parallel to the blood vessel 11) from the skin incised portion 93 toward the groin 92, and the trocar 21 is fixed.

When inserting the dissector 31, the inside of the cavity 12 is observed by using the monitor 102, the dissector 31 is slightly pushed in between a vascular connective tissue 13 and the blood vessel 11 while performing dissection without damaging the branch 11a, the dissector 31 is slightly pulled back, and the dissector 31 is gradually advanced based on this operation. Furthermore, the dissector 31 is penetrated from the knee 91 toward the groin 92 along the blood vessel 11.

When the detachment procedure using the dissector 31 is finished, the dissector 31 is removed from the trocar 21. The insertion section 54 of the rigid endoscope 51 is arranged in the rigid scope insertion channel 420 of the tube member 420a of the harvester 41, and the eyepiece portion 53 of the rigid endoscope 51 is fixed to the endoscope holding portion 400a. Moreover, the harvester 41 having the rigid endoscope 51 inserted therein is inserted into the trocar 21.

When giving the patient a treatment, the grip portion 400b of the operation portion 400 of the harvester 41 is gripped by, e.g., a right hand. As described above, in a state that the grip portion 400b which is in the distal side region in the entire region of the operation portion 400 is held, for example, the grip portion 400b can be held in such a manner that the bipolar cutter button 401 is operated with a right thumb and the vein keeper button 402, the lock button 453, and the lock button 454 are appropriately operated with an index finger, a middle finger, and an annular finger. The wiper operation ring 419 which is close to the insertion portion 42 can be rotationally moved about the central axis C with the thumb and the index finger.

Figure 14A:
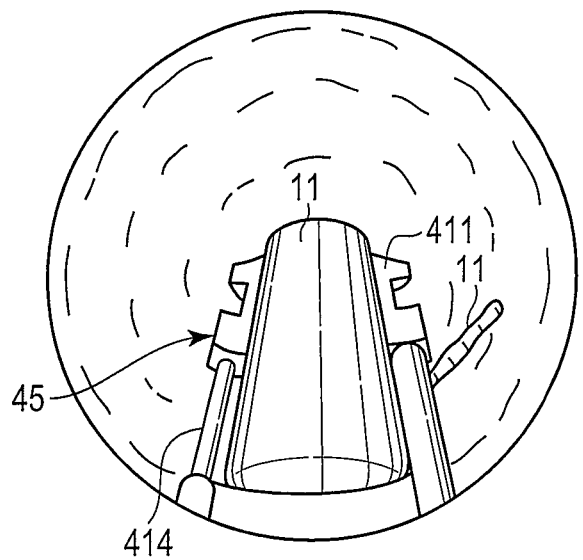
FIG. 14A is an endoscopic image showing a state that a rigid endoscope is arranged in the harvester in the vessel harvesting system according to the embodiment and the inside of a body cavity is observed.
Figure 14B:
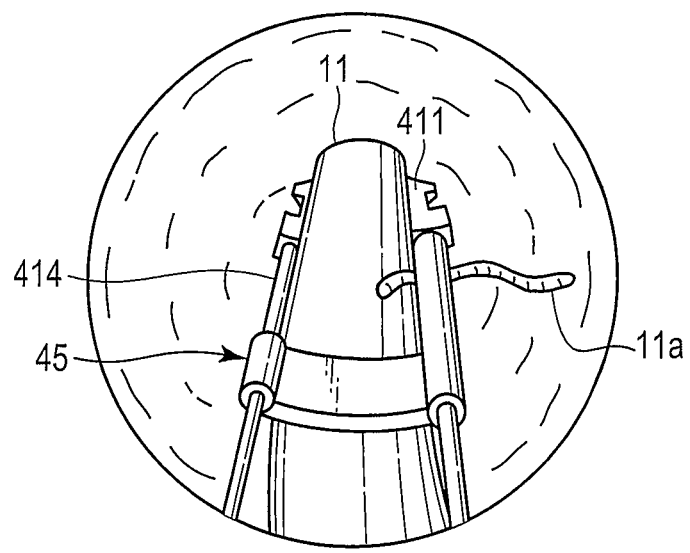
FIG. 14B is an endoscopic image showing a state that the rigid endoscope is arranged in the harvester in the vessel harvesting system according to the embodiment and the inside of the body cavity is observed.

When the vein keeper button 402 is moved forward or backward, the blood vessel holding base 411 of the vein keeper 45 moves forward or backward with respect to the distal end portion of the insertion portion 42. Thus, for example, in an endoscopic image at the time of cutting the branch 11a of the blood vessel 11 shown in FIG. 14A, if a state of the branch 11a is hard to be confirmed, the vein keeper button 402 is advanced in the longitudinal axis direction. As a result, the blood vessel holding base 411 is also moved forward from the distal end of the insertion portion 42 as shown in FIG. 14B, and such an endoscopic image as shown in FIG. 14B that is suitable for confirming a state of the branch 11a can be visually recognized. Additionally, the blood vessel 11 can be retired by the blood vessel holding base 411 in the direction away from the bipolar cutter 43 in such a manner that the bipolar cutter 43 is not brought into contact with the blood vessel 11.

In such a state, a living tissue (the branch 11a in this example) can be incised by the bipolar cutter 43 of the harvester 41, or the living tissue can be coagulated.

In case of cutting the living tissue, since the lever 72a of the switching portion 403 is being energized in the cutting mode, the lever 72a does not have to be operated. Therefore, in a state that the grip portion 400b is held with the right hand so that the bipolar cutter button 401 and the vein keeper button 402 can be operated, the bipolar cutter button 401 of the grip portion 400b is operated, the branch 11a as a cutting target is guided into the V-shaped groove 431c of the cutter main body 431 and brought into contact with the cutting electrode 433 as shown in FIG. 15A, and the vascular connective tissue 13 or the branch 11a is brought into contact with at least one of the first and second coagulation electrodes 435 and 437. This state is confirmed in an endoscopic image obtained by the rigid endoscope 51. It is to be noted that both the first and second coagulation electrodes 435 and 437 are assumed to be in contact with the vascular connective tissue 13.

After an operator confirms from an image in the monitor 102 that the branch 11a is in contact with the cutting electrode 433 and the first and second coagulation electrodes 435 and 427 are in contact with the vascular connective tissue 13, the pedal of the foot switch 109 of the electro-surgical generator 107 is depressed with a foot. At this time, a transmission path of a high-frequency current (electrical energy) is in the state shown in FIG. 6A. That is, the cutting electrode 433 is electrically connected to the pin B1 of the bipolar connector 47a, and the first, and second coagulation electrodes 435 and 437 are electrically connected to the pin B2 of the bipolar connector 47a. Therefore, the HF current flows between the cutting electrode 433 and the first and second coagulation electrodes 435 and 437 through the living tissue. Since the outer surface area of the cutting electrode 433 is smaller than the outer surface area of each of the first and second coagulation electrodes 435 and 437, current density of the cutting electrode 433 is greatly higher than current density of each of the first and second coagulation electrodes 435 and 437. Therefore, the branch 11a that is in contact with the cutting electrode 433 is cut, and a cut plane of the branch 11a is coagulated by Joule heat. At this time, the first and second coagulation electrodes 435 and 437 function as ground electrodes in a relationship of the current density between themselves and the cutting electrode 433.

It is to be noted that, in a state that the living tissue is not in contact with the cutting electrode 433 but the living tissue is in contact with both the first and second coagulation electrodes 435 and 437 when the treatment mode is the cutting mode, even if the pedal of the foot switch 109 is depressed, a HF current does not flow, and an electrical treatment is not given.

Further, when it is confirmed from the endoscopic image that the cutting the branch 11a has been finished, the foot is released from the pedal of the foot switch 109.

In this manner, as shown in FIG. 15B, a portion that the blood vessel 11 is coupled the vascular connective tissue 13 by the branch 11a is separated by cutting the branch 11a.

When the grip portion 400b is held with the right hand so that the bipolar cutter button 401 and the vein keeper button 402 can be operated, it is difficult to use the right hand to move the lever 72a of the switching portion 403 arranged at a position close to the grip portion 400b of the operation portion 400 and the endoscope holding portion 400a at the rear end of the operation portion 400 in a direction orthogonal to the axial direction of the bipolar cutter button 401 or the vein keeper button 402 (a direction crossing the axial direction). That is, it is possible to prevent the cutting mode of the switching portion 403 from being unintentionally switched to the coagulation mode.

On the other hand, when coagulating the vascular connective tissue 13 or the branch 11a that is in contact with the first and second coagulation electrodes 435 and 437, the right hand is changed to the left hand to hold the grip portion 400b of the operation portion 400, and the lever 72a is operated with the right hand. That is, when operating the lever 72a of the switching portion 403, the right hand holding the grip portion 400b is first changed to, e.g., the left hand. At this time, it is preferable to hold the grip portion 400b with the left hand so that the bipolar cutter button 401 or the vein keeper button 402 can be operated.

Furthermore, in case of operating the lever 72a, the lever 72a is operated by, e.g., pinching with fingers of the right hand. Thus, when operating the lever 72a of the switching portion 403, it is possible to prevent the cutting mode from being unintentionally switched to the coagulation mode. Moreover, energizing to the cutting mode side by the coil spring 78 also enables preventing the cutting mode from being unintentionally switched to the coagulation mode.

In case of actually coagulating the vascular connective tissue 13 or the branch 11a that is in contact with the first and second coagulation electrodes 435 and 437, a state that the grip portion 400b is gripped with the left hand is maintained, the lever 72a is rotationally moved with the right hand against an impetus of the coil spring 78, and the treatment mode of the bipolar cutter 43 is switched from the cutting mode to the coagulation mode. At this time, when the click mechanism (not shown) such as a spring click provided between, e.g., the lever 72a of the switching portion 403 and the operation portion 400 is actuated, the sense of click is transmitted to fingers of an operator who operates the lever 72a, and the operator can readily recognize that the treatment mode has been switched to the coagulation mode. Additionally, in a state that the treatment mode is the coagulation mode, the pedal of the foot switch 109 of the electro-surgical generator 107 is depressed with a foot. At this time, a transmission path of electrical energy is in the state shown in FIG. 6B. That is, the second coagulation electrode 437 is connected to the pin B1 of the bipolar connector 47a, and the first coagulation electrode 435 is connected to the pin B2 of the bipolar connector 47a. Thus, as shown in FIG. 16, the HF current flows through the first coagulation electrode 435 and the second coagulation electrode 437 via the living tissue 13 or the branch 11a that is in contact with the first coagulation electrode 435 and the second coagulation electrode 437. At this time, since the outer surface area of the first coagulation electrode 435 is substantially equal to the outer surface area of the second coagulation electrode 437 and these electrodes have substantially the same shape, the first coagulation electrode 435 and the second coagulation electrode 437 have substantially the same current density, and the living tissue 13 that is in contact with the first coagulation electrode 435 and the second coagulation electrode 437, bleeding points 13b, 13c, and 13d, or a coagulation region 13a including the branch 11a is coagulated by Joule heat.

It is to be noted that, even if the pedal of the foot switch 109 is depressed in the state that the living tissue is in contact with one of the first and second coagulation electrodes 435 and 437 when the treatment mode is the coagulation mode, the electricity does not flow.

Further, after confirming from the endoscopic image that the coagulation of the living tissue has been finished, the foot is released from the pedal of the foot switch 109.

As described above, in this embodiment, it is difficult to operate the lever 72a in the state that the grip portion 400b of the operation portion 400 is gripped with one hand, and unintentionally switching the cutting mode to the coagulation mode can be avoided.

It is to be noted that, when the right hand is released from the lever 72a, the coagulation mode is switched to the cutting mode by an energizing force of the coil spring 78. At this time, to prevent the living tissue from unintentionally coming into contact with the cutting electrode 433, the cutting electrode of the cutter main body 431 may be arranged to face the guard portion 416 as shown in FIG. 3A and FIG. 3B.

Moreover, the inside of the cavity 12 is observed by using an endoscopic image in the monitor 102, the blood vessel holding base 411 is moved closer the next branch 11a, the same procedure as that described above is repeated with the bipolar cutter 43, the branch 11a is sequentially cut, and the blood vessel 11 is separated from the vascular connective tissue 13. Then, the blood vessel 11 can be taken out from the skin incised portion 93.

It is to be noted that, when the procedure of cutting the branch 11a is repeated, the attached matter 418 (see FIG. 3C) such as blood, a mucosal membrane, or subcutaneous fat adheres to the observation surface 54b of the rigid endoscope 51, and a viewing field of the rigid endoscope 51 may be blocked depending on circumstances. In such a case, the wiper operation ring 419 can be rotationally moved by a hand and fingers while gripping the grip portion 400b of the operation portion 400, and the attached matter 418 can be scraped out.

Additionally, according to this embodiment, in both the cutting mode and the coagulation mode as the treatment mode, when at least two of the three electrodes, i.e., the cutting electrode 433, the first coagulation electrode 435, and the second coagulation electrode 437 are used, a treatment such as coagulation or a cutting can be given to the living tissue. Therefore, when the harvester 41 according to this embodiment is used, the treatments, e.g., the coagulation and the cutting can be independently given to a subject by using one endoscope treatment device (the harvester 41) without separately using the endoscope treatment device for the cutting and the endoscope treatment device for the coagulation. As a result, in this embodiment, the endoscope treatment device does not have to be removed from the trocar 21 and replaced to give different treatments like a cutting and coagulation, and hence operative duration can be reduced.

Further, in this embodiment, the cutter main body 431 of the bipolar cutter 43 arranged in the insertion portion 42 of the harvester 41 has the cutting electrode 433, the first coagulation electrode 435, and the second coagulation electrode 437. Therefore, in this embodiment, the subject can be sufficiently incised and coagulated even in a narrow body cavity.

Furthermore, in this embodiment, a necessary region can be coagulated by the first and second coagulation electrodes 435 and 437 in the coagulation mode as required.

Moreover, in this embodiment, the cutting and the coagulation are separately carried out based on a difference in area (a difference in current density) between the cutting electrode 433 and the first coagulation electrode 435 and the second coagulation electrode 437, and hence the subject can be coagulated and incised without changing an output mode (a current value).

It is to be noted that, in this embodiment, the lever 72a of the switching portion 403 is usually in the cutting mode and it can be switched to the coagulation mode against an impetus of the coil spring 78, but the coil spring 78 does not have to be provided. In this case, even if a hand is released from the lever 72a in the coagulation mode, automatically returning to the cutting mode is avoided. Moreover, although the description has been given as to the situation where the cutting mode corresponds to the positional arrangement shown in FIG. 9B and FIG. 11B, the positions shown in FIG. 9B and FIG. 11B may be set to the cutting mode, and the positions shown in FIG. 9A and FIG. 11A may be set to the coagulation mode. In this case, when switching from the cutting mode to the coagulation mode, the lever 72a set at the position shown in each of FIG. 9B and FIG. 11B is moved to the position shown in each of FIG. 9A and FIG. 11A against the energizing force of the coil spring 78.

Although the harvester 41 includes the vein keeper 45 in the above description, the vein keeper 45 does not have to be necessarily provided.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical treatment device which is used together with an endoscope, comprising:
    a sheath which includes a distal end portion, a proximal end portion, and a central axis defined by the distal end portion and the proximal end portion and which is configured to be inserted into a body cavity;
    a vein keeper which is arranged on the distal end portion of the sheath and which is configured to hold an extracted blood vessel;
    a cutter main body which is arranged on the distal end portion of the sheath and faces the vein keeper in respect to the central axis and which is configured to cut a branch of the extracted blood vessel;
    an operation portion which is arranged at the proximal end portion of the sheath and which is configured to be operated in a longitudinal direction of the sheath and is movable in the longitudinal direction of the sheath to move the vein keeper and the cutter main body, wherein the operation portion includes a central axis parallel to the central axis of the sheath;
    a first electrode which is arranged on a first surface of the cutter main body which faces the vein keeper;
    second and third electrodes which are insulated from each other and which are arranged on a second surface of the cutter main body which is an opposite side with respect to the first surface; and
    a switching portion which is arranged on a rear side of the operation portion and is configured to move in a different direction with respect to a moving direction of the operation portion, which is configured to switch between a cutting mode configured to cut the branch when a high frequency (HF) current flows through the first and second electrodes from an energy source and a coagulation mode configured to coagulate a wall portion of the body cavity when a HF current flows through the second and third electrodes from the energy source, and which is configured to prevent a same hand from operating the operation portion when one of the cutting mode and the coagulation mode is switched to the other of the cutting mode and the coagulation mode, wherein the switching portion includes an electrical segment which switches the cutting mode and the coagulation mode, and wherein the switching portion includes a drum which includes the electrical segment arranged thereon and is rotationally movable with respect to the central axis of the operation portion.

2. The surgical treatment device according to claim 1, wherein the switching portion is movable in a direction deviating from a state parallel to the central axis of the sheath.

3. The surgical treatment device according to claim 1, wherein the switching portion is movable in a direction orthogonal to the central axis of the sheath.

4. The surgical treatment device according to claim 1, wherein the switching portion includes an impetus member which energizes to maintain a state of one of the cutting mode and the coagulation mode.

5. The surgical device according to claim 1, wherein
the sheath further includes a longitudinal axis defined by the distal and end portion and the proximal end portion, and
the operation portion includes a moving member which is movable in an axial direction of the longitudinal axis of the sheath to move the cutter main body along the longitudinal axis of the sheath.

6. The surgical treatment device according to claim 1, comprising a scope holder which is arranged at a proximal end portion of the operation portion and which is configured to hold the endoscope in a state that the endoscope is aligned with the cutter main body, and
wherein the switching portion is provided between the operation portion and the scope holder.

7. The surgical treatment device according to claim 1, wherein
an area of the first electrode arranged on the first surface is smaller than each area of the second and third electrodes, and
the area of the second electrode is the same as the area of the third electrode.

8. A surgical treatment device which is used together with an endoscope, comprising:
a sheath which includes a distal end portion, a proximal end portion, and a central axis defined by the distal end portion and the proximal end portion and which is configured to be inserted into a body cavity;
a vein keeper which is arranged on the distal end portion of the sheath and which is configured to hold an extracted blood vessel;
a cutter main body which is arranged on the distal end portion of the sheath and faces the vein keeper in respect to the central axis and which is configured to cut a branch of the extracted blood vessel;
an operation portion which is arranged at the proximal end portion of the sheath and which is configured to be operated in a longitudinal direction of the sheath and is movable in the longitudinal direction of the sheath to move the vein keeper and the cutter main body, wherein the operation portion includes a central axis parallel to the central axis of the sheath;
a first electrode which is arranged on a first surface of the cutter main body which faces the vein keeper;
second and third electrodes which are insulated from each other and which are arranged on a second surface of the cutter main body which is an opposite side with respect to the first surface; and
a switching portion which is arranged on a rear side of the operation portion and is configured to move in a different direction with respect to a moving direction of the operation portion, which is configured to switch between a cutting mode configured to cut the branch when a high frequency (HF) current flows through the first and second electrodes from an energy source and a coagulation mode configured to coagulate a wall portion of the body cavity when a HF current flows through the second and third electrodes from the energy source, and which is configured to prevent a same hand from operating the operation portion when one of the cutting mode and the coagulation mode is switched to the other of the cutting mode and the coagulation mode;
wherein the switching portion includes a support member provided with the operation portion, a revolving member which is rotationally movable with respect to the central axis of the operation portion, a drum which is rotationally movable together with the revolving member, a plurality of electrical contacts which are arranged on the support member, and a plurality of drum-side contacts which are arranged on the drum and brought into contact with the electrical contacts arranged on the support member in accordance with selection of the cutting mode and the coagulation mode.

9. The surgical treatment device according to claim 8, wherein the switching portion is movable in a direction deviating from a state parallel to the central axis of the sheath.

10. The surgical treatment device according to claim 8, wherein the switching portion is movable in a direction orthogonal to the central axis of the sheath.

11. The surgical treatment device according to claim 8, wherein the switching portion includes an impetus member which energizes to maintain a state of one of the cutting mode and the coagulation mode.

12. The surgical device according to claim 8, wherein
the sheath further includes a longitudinal axis defined by the distal end portion and the proximal end portion, and
the operation portion includes a moving member which is movable in an axial direction of the longitudinal axis of the sheath to move the cutter main body along the longitudinal axis of the sheath.

13. The surgical treatment device according to claim 8, comprising a scope holder which is arranged at a proximal end portion of the operation portion and which is configured to hold the endoscope in a state that the endoscope is aligned with the cutter main body, and
wherein the switching portion is provided between the operation portion and the scope holder.

14. The surgical treatment device according to claim 8, wherein
an area of the first electrode arranged on the first surface is smaller than each area of the second and third electrodes, and
the area of the second electrode is the same as the area of the third electrode.

* * * * *